United States Patent
Ohlmann et al.

(10) Patent No.: US 11,208,392 B2
(45) Date of Patent: Dec. 28, 2021

(54) N-ALKYL-D-GLUCARO-6 AMIDE DERIVATIVES AND ALKYLAMMONIUM SALTS THEREOF AS INTERMEDIATES FOR PREPARING D-GLUCARO-6,3-LACTONE MONOAMIDE

(71) Applicant: BASF SE, Ludwigshafen am Rhein (DE)

(72) Inventors: Dominik Ohlmann, Ludwigshafen (DE); Boris Tissberger, Ludwigshafen (DE); Thomas Bodenstein, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/753,379

(22) PCT Filed: Sep. 28, 2018

(86) PCT No.: PCT/EP2018/076473
§ 371 (c)(1),
(2) Date: Apr. 3, 2020

(87) PCT Pub. No.: WO2019/068583
PCT Pub. Date: Apr. 11, 2019

(65) Prior Publication Data
US 2020/0277269 A1    Sep. 3, 2020

(30) Foreign Application Priority Data

Oct. 5, 2017 (EP) ..................................... 17194857

(51) Int. Cl.
*C07D 307/33* (2006.01)
(52) U.S. Cl.
CPC .................................. *C07D 307/33* (2013.01)
(58) Field of Classification Search
CPC .................................................. C07D 307/33
USPC ....................................................... 549/314
See application file for complete search history.

(56) References Cited

U.S. PATENT DOCUMENTS

| 2,472,168 | A | 6/1949 | Mehltretter et al. |
| 5,599,977 | A | 2/1997 | Kiely et al. |
| 6,049,004 | A | 4/2000 | Kiely et al. |
| 6,498,269 | B1 | 12/2002 | Merbouh et al. |
| 8,669,397 | B2 | 3/2014 | Boussie et al. |
| 2006/0084817 | A1 | 4/2006 | Chenault |
| 2020/0024244 | A1 | 1/2020 | Roy et al. |

FOREIGN PATENT DOCUMENTS

JP     S4310617 B1    5/1968

OTHER PUBLICATIONS

Hashimoto, Journal of Polymer Science, Part A: Polymer Chemistry (2006), 44(16), 4895-4903.*
Aury, Eur. J. Org. Chem. 2004, 2057-2066.*
Chen, J. Org. Chem. 1996, 61, 5847-5851.*
Ide, Yakugaku Zasshi (1966), 86(1), 31-6.*
International Search Report and Written Opinion for International Application No. PCT/EP2018/076473, dated Dec. 7, 2018, 15 pages.
Liang Chen et al. Synthesis of Stereoregular Head, Trail Hydroxylated nylons derived from D-Glucose, The Journal of Organic Chemistry, 61 (7), Jan. 1, 1996, pp. 5847-5851.
Aury Sabrina et al. Amphiphilic amide derivatives of D-glucaric acid. Synthesis and complexing properties toward anthanide (III) ions, European Journal of Organic Chemistry, 9, May 1, 2004, pp. 2057-2066.
Junji Ide et al. Reactions of D-Glucarolactone with Amines, Journal of the Pharmaceutical Society of Japan, 86(1), Jan. 1, 1966, pp. 31-36.
Arvind Viswanathan et al. Mechanisms for the formation of diamides and polyamides by aminolysis of D-Glucaric Acid Esters, Journal of Carbohydrate Chemistry, 22 (9), Dec. 31, 2003, pp. 903-918.
European Search Report for EP Patent Application No. 17194857.3, dated Apr. 4, 2018, 4 pages.
Fieser, et al., "Synthetic Emulsifying Agents", Journal of the American Chemical Society, vol. 78, Issue 12, Jun. 1, 1956, pp. 2825-2832.
Gehret, et al., "Convenient Large-Scale Synthesis of d-Glucaro-1,4:6,3-dilactone", The Journal of Organic Chemistry, vol. 74, Issue 21, Sep. 24, 2009, pp. 8373-8376.
Nitta, et al., "D-Glucaramide derivatives", Database CA [Online], Chemical Abstracts Service, Columbus, Ohio, US, XP002777812, STN Database accession No. 1969:11959, 3 pages.
Zinner, et al., "Lactonic acid esters and amides of D-saccharic acid", The Institute of Organic Chemistry at the University of Rostock, Mar. 12, 1956, pp. 1503-1507.

* cited by examiner

*Primary Examiner* — Nizal S Chandrakumar
(74) *Attorney, Agent, or Firm* — Armstrong Teasdale LLP

(57) ABSTRACT

Provided herein is a process for preparing D-glucaro-6,3-lactone monoamide from D-glucaro-6,3-lactone.

12 Claims, No Drawings

N-ALKYL-D-GLUCARO-6 AMIDE DERIVATIVES AND ALKYLAMMONIUM SALTS THEREOF AS INTERMEDIATES FOR PREPARING D-GLUCARO-6,3-LACTONE MONOAMIDE

CROSS-REFERENCE TO RELATED APPLICATIONS

This application is a U.S. National Phase Application of PCT/EP2018/076473, filed Sep. 28, 2018, which claims the benefit of priority to European Application No. 17194857.3, filed Oct. 5, 2017, the contents of which are hereby expressly incorporated by reference in their entirety.

DESCRIPTION

The presently claimed invention is directed to a process for preparing D-glucaro-6,3-lactone monoamide from D-glucaro-6,3-lactone.

BACKGROUND OF THE INVENTION

D-glucaric acid or saccharic acid is being widely used for preparing adipic acid by deoxydehydration reaction. In turn, adipic acid is extensively used for manufacturing nylon-6,6. The glucaric acid is commercially available, but only as an aqueous solution. This limits the reaction solvent to water or aqueous mixtures. Alternatively, salts of D-glucaric acid have also been used for manufacturing adipic acid, to meet the growing demand. However, upon manufacturing adipic acid in the presence of the salts of D-glucaric acid, several intermediates are formed, which are difficult to separate out due to their tendency to exist as a mixture. Nevertheless, these intermediates, if obtained selectively, may turn out to be reactants for important industrial chemicals.

These important intermediates are lactones, which exist in the mono- and di-form. Examples of such mono-lactones include D-glucaro-1,4-lactone and D-glucaro-6,3-lactone while D-glucaro-1,4:6,3-lactone is one such intermediate di-lactone. Further compounds such as esters, monoamides, diamides, etc. have been found to be of vital importance for various applications.

Of the above-mentioned lactones, D-glucaro-6,3-lactone is an industrially important mono-lactone of D-glucaric acid. The commercial availability of D-glucaro-6,3-lactone is very limited or almost nil and hence the compounds obtained therefrom are also limited. The ability of this particular mono-lactone to be used for manufacturing various acids, esters, alcohols, amides, etc. has led to developments in arriving at various means for its selective production. In fact, it is due to the potential of the compounds derived from this monolactone, particularly of the mono-amides, that various researchers are looking for viable methods to obtain them.

Acidification of calcium D-glucarate tetrahydrate with sulfuric acid in the presence of acetone-water is discussed by Troy et.al. [J. Org. Chem. 2009, 74, 8373-8376]. The acidification step is followed by filtration, reduced pressure operation and concentration steps to finally obtain a concentrated aqueous solution containing solid particles of a mixture of D-glucaric acid, D-glucaro-1,4-lactone, D-glucaro-6,3-lactone and D-glucaro-1,4:6,3-lactone in a fixed ratio.

Hydrophobic derivatives of D-glucaric acid, HOOC—(CHOH)$_4$—CONHR, where R is an alkyl chain having 3, 8, 10, or 12 carbon atoms, have been synthesized from D-glucaro-1,4-lactone and the corresponding amines by Rubini et.al. [Eur. J. Org. Chem. 2004, 2057-2066]. The complexing abilities of these compounds toward trivalent lanthanide cations have been studied, using the water-soluble propyl compound, and compared to that of gulonic acid, which corresponds to the complexing part of these molecules. The formation constants of the complexes have been determined and their structures discussed. The surfactant properties of the $C_8$, $C_{10}$ and $C_{12}$ glucaramides and their extracting ability toward $Ln^{III}$ ions have also been evaluated.

Diamides of D-saccharic acid are discussed by Zinner et.al. [Chem Ber 1956, 1503]. The esterification of saccharic lactonic (3,6) acid with alcohols produces the lactone ring. Saccharic lactonic acid esters, which are characterized as tribenzoates and tris-p-nitrobenzoates, are obtained. The lactone ring is cleaved by aliphatic and aromatic amines, forming saccharic acid diamides.

Long chain alkylglucaramides (C12 to C18) from N-alkylglucoronamides by bromine oxidation is discussed by Fieser et.al. [J. Am. Chem. Soc. 1956, 78, 2825-2832]. Various synthetic compounds containing both lipophilic and hydrophilic groups have been prepared and their emulsifying properties have been examined. Conjugates of various amino acids with stearylamine, n—$C_{18}H_{37}$NHCOCH(R)NH$_2$ have been found to have promising emulsifying properties. This contrasts with peptides of the type $C_{17}H_{35}$CONHCH(R)COOH which are, at the most, weak emulsifying agents.

Reaction of D-glucaro-1,4-lactone or 6,3-lactone with amines to obtain glucaramide derivatives is discussed by Nitta Yoshihiro et.al. ["D-Glucaramide derivatives" obtained from Chemical Abstract Service, Columbus, Ohio].

Junji Ide et.al. [Journal of Pharmaceutical Society of Japan, vol. 86, no. 1, 1 Jan. 1966, pages 31-36] discuss the reaction of D-glucaro-6,3-lactone with benzylamine, butyl amine or cyclohexylamine in 50% aq. methanol to afford the corresponding N-benzyl-D-glucar-6-amide benzylamine salt, N-butyl-D-glucar-6-amide butylamine salt and N-cyclohexyl-D-glucar-6-amide cyclohexylamine salt.

Arvind Vishwanathan et.al. [J. of Carbohydrate Chemistry, vol. 22, no. 9, 31 Dec. 2003, pages 903-918] discuss the reaction of ethyl D-glucarate-6,3-lactone with n-propylamine to obtain N,N'-dipropyl-D-glucaramide.

The existing techniques for selectively obtaining the D-glucaro-6,3-lactone monoamide are either not available at all or if available, they are not satisfactory in terms of low yield and purity of final product. Moreover, the relatively high yield and selectivity of undesirable products such as other mono- and di-lactone, diamides and acid renders the available techniques unfavourable.

Thus, it was an objective of the presently claimed invention to provide a process for selectively preparing the D-glucaro-6,3-lactone monoamide having a high purity with process conditions which render the invention economical by optimizing them in a manner that the yield of the D-glucaro-6,3-lactone monoamide is selectively maximized with minimum formation of diamides, other mono- and di-lactone as well as acid.

SUMMARY OF THE INVENTION

Surprisingly, it has been found that the reaction between a salt of D-glucaro-6,3-lactone and an amine of general formula (I) at a temperature in the range of $\geq 40°$ C. to $\leq 90°$ C., followed by treatment with an acid result in a high yielding process to produce the D-glucaro-6,3-lactone monoamide. The optimized process conditions of the present invention provide a selective process for preparing the D-glucaro-6,3-lactone monoamide at high yield and with minimum formation of diamides, other mono- and di-lactone as well as acid.

Accordingly, in one aspect, the presently claimed invention is directed to a process for preparing the D-glucaro-6,3-lactone monoamide, comprising the steps of:

A) adding an amine of general formula (I)

wherein $R_1$ denotes unsubstituted, linear or branched, alkyl or alkenyl having 4 to 22 carbon atoms, to an aqueous solution of a salt of D-glucaro-6,3-lactone and heating at a temperature in the range of ≥40° C. to ≤90° C., to obtain a compound of general formula (II)

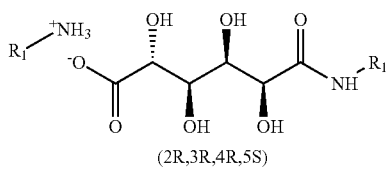

wherein, $R_1$ denotes unsubstituted, linear or branched, alkyl or alkenyl having 4 to 22 carbon atoms, and B) treating the compound of general formula (II) with an acid to obtain a compound of general formula (III)

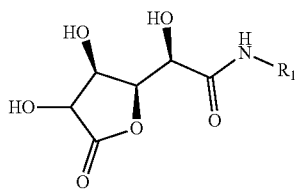

wherein, $R_1$ denotes unsubstituted, linear or branched, alkyl or alkenyl having 4 to 22 carbon atoms.

In another aspect, the presently claimed invention is directed to a compound of general formula (II)

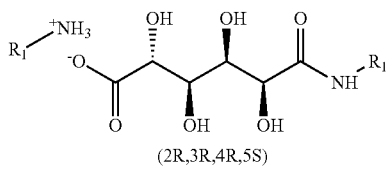

wherein, $R_1$ denotes unsubstituted, linear or branched, alkyl or alkenyl having 4 to 22 carbon atoms.

In yet another aspect, the presently claimed invention is directed to a compound of general formula (III)

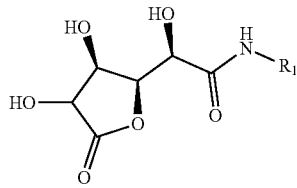

wherein, $R_1$ denotes unsubstituted, linear or branched, alkyl or alkenyl having 4 to 22 carbon atoms.

In still another aspect, the presently claimed invention is directed to the use of the compound of general formula (III) above or obtained according to the process above, as surfactant, emulsifier, solubilizer, rheology modifier and gelator.

DETAILED DESCRIPTION OF THE INVENTION

Before the present compositions and formulations of the invention are described, it is to be understood that this invention is not limited to particular compositions and formulations described, since such compositions and formulation may, of course, vary. It is also to be understood that the terminology used herein is not intended to be limiting, since the scope of the present invention will be limited only by the appended claims.

If hereinafter a group is defined to comprise at least a certain number of embodiments, this is meant to also encompass a group which preferably consists of these embodiments only. Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(A)", "(B)" and "(C)" or "(a)", "(b)", "(c)", "(d)", "i", "ii" etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Oxidation of aldoses, for instance, with bromine-water affects only the aldehyde group, converting it into a carboxyl group. By the term "aldose", it is referred to a monosaccharide containing only one aldehyde group per molecule. The oxidation products are called aldonic acids, for example D-gluconic acid is obtained from D-glucose. When aldoses are oxidized using strong oxidizing agents, for example with concentrated nitric acid, the primary alcohol group as well as the aldehyde group are transformed into carboxyl groups. The products are polyhydroxydicarboxylic acids known as aldaric acids.

An example of aldaric acid is the aldaric acid derived from glucose, i.e. D-glucaric acid, also known as saccharic acid. Conventional techniques may be employed for obtaining the D-glucaric acid. Such techniques are known to a person skilled in the art. Nevertheless, U.S. Pat. No. 2,472,168 illustrates a method for the preparation of the D-glucaric acid from the glucose using a platinum catalyst in the presence of oxygen and a base. Other oxidation methods, as disclosed in U.S. Pat. Nos. 6,049,004, 5,599,977, 6,498,269 and 8,669,397, may also be employed.

D-glucaro-6,3-lactone can also be obtained by various available techniques. One such technique is discussed by Chen and Kiely [J. Org. Chem. 1996, 61, 5847-5851], wherein a cation exchange resin is added to a mixture of monopotassium D-glucarate and water. Acid form of the cation exchange resin is added further, with filtration and concentration carried out thereafter. D-glucaro-6,3-lactone is obtained after 2-3 days of crystallization in the form of white solids and used for synthesis of head-tail hydroxylated nylons. Troy et. Al. [J. Org. Chem. 2009, 74, 8373-8376] disclose the acidification of calcium D-glucarate tetrahydrate with sulfuric acid in acetone-water solvent system. The acidification step is followed by filtration, reduced pressure operation and concentration steps to finally obtain a concentrated aqueous solution containing solid particles of a mixture of D-glucaric acid, D-glucaro-1,4-lactone, D-glucaro-6,3-lactone and D-glucaro-1,4:6,3-lactone in a fixed ratio. For the purpose of the present invention, the choice of the D-glucaro-6,3-lactone is not limited to the method used to prepare the same. A person skilled in the art is aware of such methods and may employ any of the available techniques to obtain the same.

Accordingly, a process for preparing the D-glucaro-6,3-lactone monoamide, comprises the steps of:
A) adding an amine of general formula (I)

$$R_1-NH_2 \qquad (I),$$

wherein,
$R_1$ denotes unsubstituted, linear or branched, alkyl or alkenyl having 4 to 22 carbon atoms, to an aqueous solution of a salt of D-glucaro-6,3-lactone and heating at a temperature in the range of ≥40° C. to ≤90° C., to obtain a compound of general formula (II)

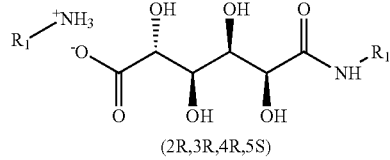

wherein,
$R_1$ denotes unsubstituted, linear or branched, alkyl or alkenyl having 4 to 22 carbon atoms, and
B) treating the compound of general formula (II) with an acid to obtain a compound of general formula (III)

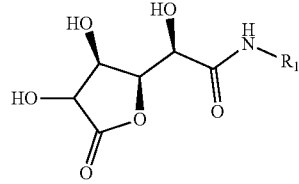

wherein,
$R_1$ denotes unsubstituted, linear or branched, alkyl or alkenyl having 4 to 22 carbon atoms.

By the term "alkyl", as used herein, it is referred to saturated hydrocarbon radical denoted by a general formula $C_nH_{2n+1}$ and wherein n is the number of carbon atoms in the range of ≥4 to ≤22.

By the term "alkenyl", as used herein, it is referred to a singly unsaturated hydrocarbon radical denoted by a general formula $C_nH_{2n+1}$ and wherein n is the number of carbon atoms in the range of ≥4 to ≤22.

For the purpose of the present invention, the salt of D-glucaro-6,3-lactone is selected from the group consisting of calcium glucaro-6,3-lactone, potassium glucaro-6,3-lactone, sodium glucaro-6,3-lactone, lithium glucaro-6,3-lactone and magnesium glucaro-6,3-lactone. The choice of such salts is not limited to the method used to prepare the same. A person skilled in the art is aware of such methods and may employ any of the available techniques to obtain the same. Preferably the salt of D-glucaro-6,3-lactone is selected from the group consisting of calcium glucaro-6,3-lactone, potassium glucaro-6,3-lactone, sodium glucaro-6,3-lactone and lithium glucaro-6,3-lactone. More preferably, it is selected from the group consisting of potassium glucaro-6,3-lactone, sodium glucaro-6,3-lactone and lithium glucaro-6,3-lactone. Most preferably, it is selected from the group consisting of sodium glucaro-6,3-lactone and lithium glucaro-6,3-lactone. In a particularly preferred embodiment, the salt of D-glucaro-6,3-lactone is sodium glucarolactone.

By the term "aqueous solution", it is referred to the solution of the salt of D-glucaro-6,3-lactone prepared by dissolving it in water. The aqueous solution is optionally stirred in order to get a homogenous mixture. By the term "stirred", it is referred to mechanical stirring using any suitable stirrer known to a person skilled in the art. The preparation of the aqueous solution not limited by the duration, type and rotational speed of the stirrer employed therein. These parameters are well-known to the person skilled in the art. However, typically the rotational speed in the range of 100 rpm to 1000 rpm for a period in the range of ≥0.1 h to ≤24 h is provided.

The aqueous solution has a weight ratio between water and the salt of D-glucaro-6,3-lactone in the range of ≥1:1 to ≤15:1. It is always preferable to use water in excess of the salt. Nevertheless, preferably the weight ratio is in the range of ≥1:1 to ≤14.8:1, or ≥1.2:1 to ≤14.8:1, or ≥1.2:1 to ≤14.4:1, or ≥1.4:1 to ≤14.4:1, or ≥1.4:1 to ≤14:1, or ≥1.6:1 to ≤14:1, or ≥1.6:1 to ≤13.8:1, or ≥1.8:1 to ≤13.8:1, or ≥1.8:1 to ≤13.4:1, or ≥2:1 to ≤13.4:1. More preferably, the weight ratio is in the range of ≥2:1 to ≤13:1, or ≥2.2:1 to ≤13:1, or ≥2.2:1 to ≤12.8:1, or ≥2.4:1 to ≤12.8:1, or ≥2.4:1 to ≤12.4:1, or ≥2.6:1 to ≤12.4:1, or ≥2.6:1 to ≤12:1, or ≥2.8:1 to ≤12:1, or ≥2.8:1 to ≤11.8:1, or ≥3:1 to ≤11.8:1, or ≥3:1 to ≤11.4:1, or ≥3.2:1 to ≤11.4:1. Most preferably, it is in the range of ≥3.2:1 to ≤11:1, or ≥3.4:1 to ≤11:1, or ≥3.4:1 to ≤10.8:1, or ≥3.6:1 to ≤10.8:1, or ≥3.6:1 to ≤10.4:1, or ≥3.8:1 to ≤10.4:1, or ≥3.8:1 to ≤10:1, or ≥4:1 to ≤10:1, or ≥4:1 to ≤9.8:1, or ≥4.2:1 to ≤9.8:1, or ≥4.2:1 to ≤9.4:1, or ≥4.4:1 to ≤9.4:1, or ≥4.4:1 to ≤9:1, or ≥4.6:1 to ≤9:1, or ≥4.6:1 to ≤8.8:1, or ≥4.8:1 to ≤8.8:1, or ≥4.8:1 to ≤8.4:1, or ≥5:1 to ≤8.4:1. In a particularly preferred embodiment, the aqueous solution of the salt of D-glucaro-6,3-lactone has a weight ratio between water and the salt of D-glucaro-6,3-lactone in the range of ≥5:1 to ≤8:1.

In step (A) of the process described hereinabove, the aqueous solution of the salt of D-glucaro-6,3-lactone is added to the amine of general formula (I)

wherein,

R1 denotes unsubstituted, linear or branched, alkyl or alkenyl having 4 to 22 carbon atoms.

The addition of the aqueous solution of the salt of D-glucaro-6,3-lactone to the amine of general formula (I) may be carried out by any suitable methods known to a person skilled in the art. For instance, the addition of the aqueous solution of the salt of D-glucaro-6,3-lactone to the amine of general formula (I) may be carried out in, such as but not limited to, a mixer. Suitable rotational speed or rpm of the mixer are known to the person skilled in this art. The adding of the aqueous solution of the salt of D-glucaro-6,3-lactone to the amine of general formula (I) is not limited to the sequence chosen therefore. That is, to say, the aqueous solution may be added all at once to the amine of general formula (I) or drop by drop or after regular intervals.

For the purpose of the present invention, $R_1$, as used herein, denotes unsubstituted, linear or branched, alkyl or alkenyl having 4 to 22 carbon atoms.

Preferably, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

The molar ratio between the amine of general formula (I) and the aqueous solution of the salt of D-glucaro-6,3-lactone, as described hereinabove in step (A), is in the range of ≥1:1 to ≤10:1. Preferably, the molar ratio is in the range of ≥1:1 to ≤9.8:1, or ≥1:1 to ≤9.6:1, or ≥1:1 to ≤9.4:1, or 1:1 to 9.2:1, or 1:1 to ≤9:1, or ≥1:1 to ≤8.8:1, or ≥1:1 to ≤8.6:1, or ≥1:1 to ≤8.4:1, or ≥1:1 to ≤8.2:1, or ≥1:1 to ≤8:1. More preferably, it is in the range of ≥1:1 to ≤7.8:1, or ≥1:1 to ≤7.6:1, or ≥1:1 to ≤7.4:1, or ≥1:1 to ≤7.2:1, or ≥1:1 to ≤7:1, or ≥1:1 to ≤6.8:1, or ≥1:1 to ≤6.6:1, or 1:1 to 6.4:1, or 1:1 to 6.2:1, or 1:1 to 6:1, or 1:1 to 5.8:1, or 1:1 to ≤5.6:1, or ≥1:1 to ≤5.4:1. Most preferably, the ratio is in the range of, or ≥1:1 to ≤5.2:1, or ≥1:1 to ≤5:1, or ≥1:1 to ≤4.8:1, or ≥1:1 to ≤4.6:1, or ≥1:1 to ≤4.4:1, or ≥1:1 to ≤4.2:1, or ≥1:1 to ≤4:1, or ≥1:1 to ≤3.8:1, or ≥1:1 to ≤3.6:1, or ≥1:1 to ≤3.4:1, or ≥1:1 to ≤3.2:1, or ≥1:1 to ≤3:1, or ≥1:1 to ≤2.8:1, or ≥1:1 to ≤2.6:1, or ≥1:1 to ≤2.4:1, or ≥1:1 to ≤2.2:1. In an embodiment, the molar ratio between the amine of general formula (I) and the aqueous solution of the salt of D-glucaro-6,3-lactone is in the range of ≥1:1 to ≤2:1.

A temperature in the range of ≥5° C. to ≤30° C. is provided for a duration in the range of ≥0.1 h to ≤5 h while adding the amine of general formula (I) to the aqueous solution of the salt of D-glucaro-6,3-lactone in step (A), as described hereinabove. Preferably, the temperature is in the range of ≥5° C. to ≤26° C., or ≥6° C. to ≤26° C. for 0.1 h to ≤4.5 h, or ≥0.1 h to ≤4 h. More preferably, in the range of ≥6° C. to ≤24° C., or ≥7° C. to ≤24° C. for 0.2 h to ≤4 h, or ≥0.2 h to ≤3.5 h. Most preferably, in the range of ≥7° C. to ≤20° C., or ≥7° C. to ≤16° C. for 0.2 h to ≤3 h, or ≥0.2 h to ≤2.5 h. Particularly preferably, the temperature is in the range of ≥8° C. to ≤16° C. for a duration in the range of ≥0.2 h to ≤2 h.

In an embodiment, the amine of general formula (I) in step (A) of the process described hereinabove, may not require any solvent. This would result in high heat generation due to the exothermic nature of the reaction between the amine of general formula (I) and the aqueous solution of the salt of D-glucaro-6,3-lactone. Heat removal in this case would be difficult to achieve. Moreover, since the compound of general formula (II) obtained in step (A) is a solid compound, it would be difficult to perform the step (A) in the absence of any solvent, such as the one described hereinbelow.

In a particularly preferable embodiment, the amine of general formula (I) is present as a mixture with at least one polar solvent. For the purpose of step (A) of the process described hereinabove, the term "amine of general formula (I)" refers to a mixture of the amine of general formula (I), as described hereinabove, and the at least one polar solvent, as described hereinbelow. By the term "at least one polar solvent", it is to be understood that the amine of general formula (I) may comprise either one or more than one, e.g. two or three, polar solvents. However, it is preferred that the amine of general formula (I) comprises only one polar solvent. Accordingly, in preferred embodiments of the present invention, the term "at least one polar solvent" is to be understood as "a polar solvent" or "one polar solvent".

For the purpose of the present invention, the at least one polar solvent is selected from the group consisting of ethers and alcohols. The terms "ethers" and "alcohols" refer to ether solvents and alcohol solvents, respectively. The at least one polar solvent in the mixture with the amine of general formula (I) in step (A) is at least one alcohol solvent. Accordingly, the term "at least one polar solvent" in the step (A), as described hereinabove or hereinbelow, is to be meant to refer to at least one alcohol solvent. By the term "at least one alcohol solvent", it is to be understood that the amine of general formula (I) may comprise either one or more than one, e.g. two or three, alcohol solvents. However, it is preferred that the amine of general formula (I) comprises only one alcohol solvent. Accordingly, in preferred embodiments of the present invention, the term "at least one alcohol solvent" is to be understood as "an alcohol solvent" or "one alcohol solvent".

The at least one alcohol in step (A) is selected from the group consisting of ethanol, methanol, n-butanol, iso-butanol, sec-butanol, n-propanol, iso-propanol, pentanol and hexanol. In an embodiment, the at least one alcohol is methanol.

The weight ratio between the at least one polar solvent or the at least one alcohol and the amine of general formula (I) in step (A) is in the range of ≥1:5 to ≤5:1. Preferably, the ratio is in the range of ≥1:4.8 to ≤5:1, or ≥1:4.8 to ≤4.8:1, or ≥1:4.4 to ≤4.8:1, or ≥1:4.4 to ≤4.4:1, or ≥1:4 to 4.4:1. More preferably, it is in the range of ≥1:4 to ≤4:1, or ≥1:3.8 to ≤4:1, or ≥1:3.8 to ≤3.8:1, or ≥1:3.4 to ≤3.8:1, or ≥1:3.4 to ≤3.4:1. Most preferably, in the range of ≥1:3 to ≤3.4:1, or 1:3 to ≤3:1, or ≥1:2.8 to ≤3:1, or ≥1:2.8 to ≤2.8:1, or ≥1:2.4 to ≤2.8:1, or ≥1:2.4 to ≤2.4:1, or ≥1:2 to ≤2.4:1. In an embodiment, the weight ratio between the at least one polar solvent or the at least one alcohol and the amine of general formula (I) in step (A) is in the range of ≥1:2 to ≤2:1.

In one embodiment, the step (A) results in the formation of the compound of general formula (II)

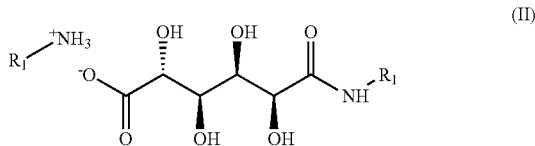

(II)

wherein, $R_1$ denotes unsubstituted, linear or branched, alkyl or alkenyl having 4 to 22 carbon atoms.

The compound of general formula (II) is a colourless solid with low solubility in water and most organic solvents except ether solvents such as tetrahydropyran and tetrahydrofuran, and acids, such as glacial acetic acid.

In an embodiment, this step of obtaining the compound of general formula (II) is carried out by:
(A1) heating a mixture comprising the amine of general formula (I) and the aqueous solution of the salt of D-glucaro-6,3-lactone at a temperature in the range of ≥40° C. to ≤90° C. to obtain a precipitate,
(A2) filtrating the precipitate of step (A1) and washing with the at least one polar solvent to obtain a crude mixture and a mother liquor,
(A3) optionally storing the mother liquor of step (A2) at a temperature in the range of ≥0° C. to ≤30° C. for a period in the range of ≥8 h to ≤15 h to obtain the crude mixture, and
(A4) drying the crude mixture of step (A2) or optionally step (A3) to obtain the compound of general formula (II).

The amine of general formula (I) and the aqueous solution of the salt of D-glucaro-6,3-lactone form a mixture upon adding. This mixture is heated to a temperature in the range of ≥40° C. to 90° C. to obtain a precipitate, as described hereinabove in step (A1). Alternatively, the step (A1) as described hereinabove may be also referred to as the heating step. Preferably, the temperature in step (A1) is in the range of ≥45° C. to ≤90° C., or ≥45° C. to ≤85° C. More preferably, it is in the range of ≥50° C. to ≤85° C., or ≥55° C. to ≤85° C. Most preferably, the temperature is in the range of ≥60° C. to ≤85° C., or ≥65° C. to ≤85° C. In an embodiment, the heating in step (A1) is carried out at a temperature in the range of ≥65° C. to ≤80° C.

For the purpose of carrying out the heating in step (A1), any suitable techniques can be used. The heating in step (A1) is not limited to the techniques selected for carrying out the said purpose. A person skilled in the art is aware of such techniques. Furthermore, the heating in heating step is also not limited to the manner in which it is carried out. For instance, the mixture may be heated continuously for a duration in the range of, such as but not limited to, ≥0.1 h to ≤24 h. Optionally, the mixture comprising the amine of general formula (I) and the aqueous solution of the salt of D-glucaro-6,3-lactone during heating in step (A1), as described hereinabove, may be stirred. By the term "stirred", it is referred to mechanical stirring using any suitable stirrer known to a person skilled in the art. The heating in step (A1) is also not limited by the duration, type and rotational speed of the stirrer employed therein. These parameters are well-known to the person skilled in the art. However, typically the rotational speed in the range of ≥100 rpm to ≤1000 rpm for a period in the range of ≥0.1 h to ≤24 h is provided.

In a preferred embodiment, the heating at a temperature in the range of ≥40° C. to ≤90° C., as described hereinabove, results in the reaction between the amine of general formula (I) and the salt of D-glucaro-6,3-lactone, thereby obtaining the compound of general formula (II) as precipitate in the step (A1). The temperature in the range of ≥40° C. to ≤90° C. ensures that formation of only D-glucaro-6,3-lactone monoamide or the compound of general formula (III) is maximised with minimum formation of diamides, other mono- and di-lactone. In particular, D-glucaro-1,4-lactone, which exists in equilibrium with the D-glucaro-6,3-lactone, forms the corresponding amide faster than the latter, especially at this temperature range. Therefore, once the 1,4-lactone is all reacted, the 6,3-lactone reacts and forms the corresponding amide, which is selectively obtained in the step (B) as compound of general formula (III).

The precipitate obtained in the heating step or step (A1) is filtered and washed in step (A2) to obtain a crude mixture and a mother liquor. Hereinafter, the step (A2) may also be interchangeably referred to as the filtration and washing step.

The precipitate obtained in the heating step still contains some quantity of reactants left unreacted as an impurity. Optionally, there might also be some other by-products present that may have been formed. To remove these unreacted impurities and/or by-products from the precipitate, filtration is carried out using any suitable filter media known to a person skilled in the art, such as but not limited to, Whatman filter paper and glass filter. Although, a substantial portion of these unreacted impurities and/or by-products pass through the filter media, some amount might still be left along with the precipitate and is collected on the filter media as residue. The residue is now washed with the at least one polar solvent, preferably the at least one alcohol solvent, as described hereinabove, at a temperature in the range of ≥5° C. to ≤30° C.

For the purpose of washing the residue in step (A2), the weight ratio between the at least one polar solvent and the precipitate is in the range of ≥1:15 to ≤15:1. It is usually preferred to keep an excess of the at least one polar solvent to dissolve the unwanted and the unreacted impurities and/or by-products, thereby obtaining the mother liquor. However, it is also possible that some amount of the precipitate along with these impurities is carried to the mother liquor. In order to recover the precipitate from the mother liquor and to increase the overall yield of the D-glucaro-6,3-lactone monoamide, hereinafter also interchangeably referred as the desired product, the mother liquor is optionally stored at a temperature in the range of ≥0° C. to ≤30° C. for a period in the range of ≥8 h to ≤15 h to obtain the crude mixture, as evident in step (A3) described hereinabove. Hereinafter, the step (A3) may also be interchangeably referred to as the storing step.

Preferably, temperature in the step (A3) is in the range of ≥0° C. to ≤26° C., or ≥0° C. to ≤22° C. More preferably, it is in the range of ≥0° C. to ≤20° C., or ≥0° C. to ≤16° C., or ≥0° C. to ≤12° C. Most preferably, it is in the range of ≥0° C. to ≤10° C., or ≥0° C. to ≤6° C. In an embodiment, the temperature in step (A3) is in the range of ≥0° C. to ≤5° C. Typically, the duration for which the temperature in step (A3) is provided, as described hereinabove, is in the range of ≥8 h to ≤14 h to obtain the crude mixture. More preferably, it is in the range of ≥8 h to ≤13 h. Most preferably, it is in the range of ≥8 h to ≤12. In an embodiment, the mother liquor is stored at the temperature described hereinabove for the period in the range of ≥8 h to ≤11 h to obtain the crude mixture.

The crude mixture obtained in the filtration and washing step i.e. step (A2) or optionally in the storing step i.e. step (A3) is subjected to drying in step (A4) to obtain the compound of general formula (II). Hereinafter, the step (A4) may be interchangeably referred to as the drying step. The drying step is performed under vacuum conditions to obtain the compound of general formula (II). By the term "vacuum conditions", it is referred to sub-atmospheric conditions of pressure.

The drying step may be performed by means of any suitable equipment known to a person skilled in the art which operate under vacuum conditions. These suitable equipments may be, such as but not limited to, rotary evaporators. The choice of a particular rotary evaporator should be made based on the desired conditions of temperature and pressure, as described hereinbelow.

For the purpose of the present invention, the drying step is performed by evaporation which is carried out at reduced pressures, preferably under vacuum conditions. The vacuum pressure is maintained in the range of ≥0.1 mbar to ≤500 mbar. Preferably, the vacuum pressure is in the range of ≥0.1 mbar to ≤480 mbar. More preferably the vacuum pressure is in the range of ≥0.1 mbar to ≤460 mbar. Most preferably the vacuum pressure is in the range of ≥0.1 mbar to ≤450 mbar.

Typically, the temperature in the drying step is in the range of ≥20° C. to ≤80° C. Preferably the temperature is in the range of ≥30° C. to ≤80° C. More preferably the temperature is in the range of 30° C. to ≤75° C. Most preferably the temperature is in the range of ≥40° C. to ≤75° C.

Typically, a duration in the range of ≥1 h to ≤55 h is provided during the drying step. Preferably the duration is in the range of ≥2 h to ≤45 h. More preferably the duration is in the range of ≥3 h to ≤35 h. Most preferably the duration is in the range of ≥4 h to ≤25 h.

In case the desired yield of the compound of general formula (II) is as per the requirement, the following temporal sequence of the steps applies (A1)→(A2)→(A4). However, in case it is less than the desired value, the following temporal sequence of the steps applies (A1)→(A2)→(A3)→(A4).

In the compound of general formula (II), $R_1$ denotes unsubstituted, linear or branched, alkyl or alkenyl having 4 to 22 carbon atoms. Preferably, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (II) obtained in step (A) is hexylammonium hexylglucaramide (II)(a), also interchangeably referred as hexylammonium (2R,3R,4R,5S)-6-(hexylamino)-2,3,4,5-tetrahydroxy-6-oxohexanoate, and is represented as shown hereinbelow

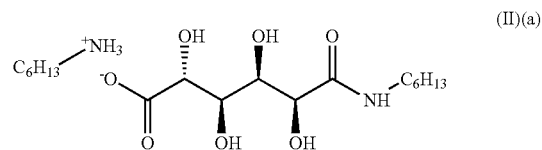

(II)(a)

In another embodiment, the compound of general formula (II) obtained in step (A) is heptylammonium heptylglucaramide (II)(b), also interchangeably referred as heptylammonium (2R,3R,4R,5S)-6-(heptylamino)-2,3,4,5-tetrahydroxy-6-oxohexanoate, and is represented as shown hereinbelow

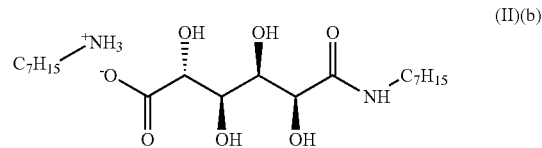

(II)(b)

In another embodiment, the compound of general formula (II) obtained in step (A) is octylammonium octylglucaramide (II)(c), also interchangeably referred as octylammonium (2R,3R,4R,5S)-6-(octylamino)-2,3,4,5-tetrahydroxy-6-oxohexanoate, and is represented as shown hereinbelow

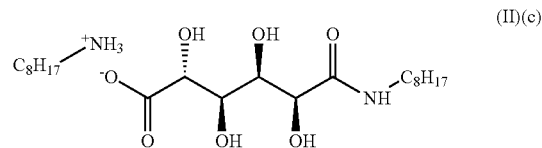

(II)(c)

In another embodiment, the compound of general formula (II) obtained in step (A) is nonylammonium nonylglucaramide (II)(d), also interchangeably referred as nonylammonium (2R,3R,4R,5S)-6-(nonylamino)-2,3,4,5-tetrahydroxy-6-oxohexanoate, and is represented as shown hereinbelow

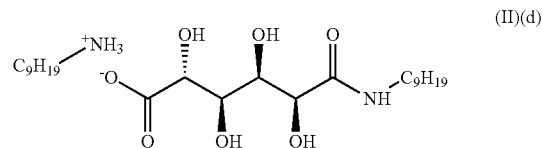

(II)(d)

In another embodiment, the compound of general formula (II) obtained in step (A) is decylammonium decylglucaramide (II)(e), also interchangeably referred as decylammonium (2R,3R,4R,5S)-6-(decylamino)-2,3,4,5-tetrahydroxy-6-oxohexanoate, and is represented as shown hereinbelow

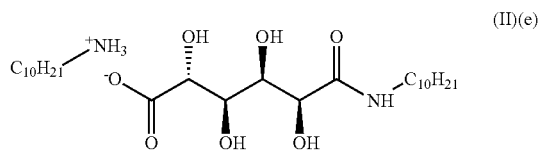

(II)(e)

In another embodiment, the compound of general formula (II) obtained in step (A) is undecylammonium undecylglucaramide (II)(f), also interchangeably referred as undecylammonium (2R,3R,4R,5S)-6-(undecylamino)-2,3,4,5-tetrahydroxy-6-oxohexanoate, and is represented as shown hereinbelow

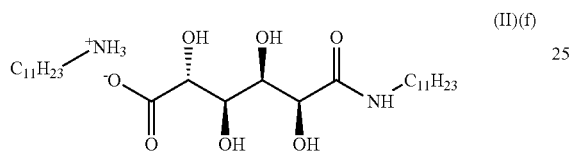

(II)(f)

In another embodiment, the compound of general formula (II) obtained in step (A) is dodecylammonium dodecylglucaramide (II)(g), also interchangeably referred as dodecylammonium (2R,3R,4R,5S)-6-(dodecylamino)-2,3,4,5-tetrahydroxy-6-oxohexanoate, and is represented as shown hereinbelow

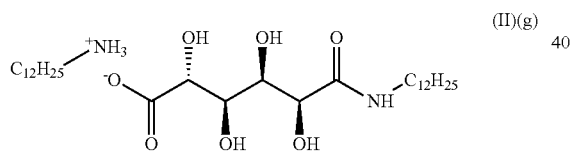

(II)(g)

In another embodiment, the compound of general formula (II) obtained in step (A) is tridecylammonium tridecylglucaramide (II)(h), also interchangeably referred as tridecylammonium (2R,3R,4R,5S)-6-(tridecylamino)-2,3,4,5-tetrahydroxy-6-oxohexanoate, and is represented as shown hereinbelow

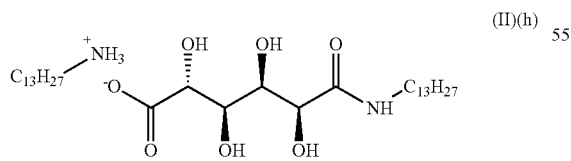

(II)(h)

In another embodiment, the compound of general formula (II) obtained in step (A) is tetradecylammonium tetradecylglucaramide (II)(i), also interchangeably referred as tetradecylammonium (2R,3R,4R,5S)-6-(tetradecylamino)-2,3,4, 5-tetrahydroxy-6-oxohexanoate, and is represented as shown hereinbelow

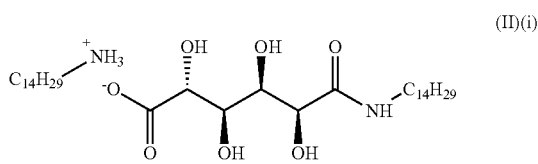

(II)(i)

In another embodiment, the compound of general formula (II) obtained in step (A) is pentadecylammonium pentadecylglucaramide (II)(j), also interchangeably referred as pentadecylammonium (2R,3R,4R,5S)-6-(pentadecylamino)-2,3,4,5-tetrahydroxy-6-oxohexanoate, and is represented as shown hereinbelow

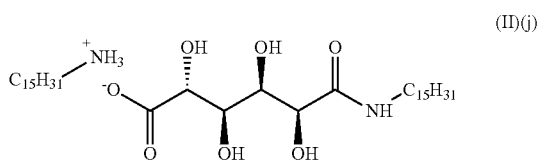

(II)(j)

In another embodiment, the compound of general formula (II) obtained in step (A) is hexadecylammonium hexadecylglucaramide (II)(k), also interchangeably referred as hexadecylammonium (2R,3R,4R,5S)-6-(hexadecylamino)-2,3,4, 5-tetrahydroxy-6-oxohexanoate, and is represented as shown hereinbelow

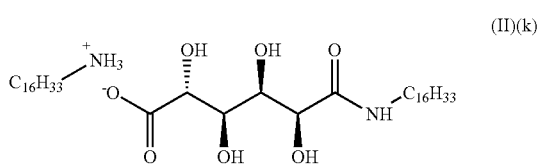

(II)(k)

In another embodiment, the compound of general formula (II) obtained in step (A) is heptadecylammonium heptadecylglucaramide (II)(l), also interchangeably referred as heptadecylammonium (2R,3R,4R,5S)-6-(heptadecylamino)-2,3,4,5-tetrahydroxy-6-oxohexanoate, and is represented as shown hereinbelow

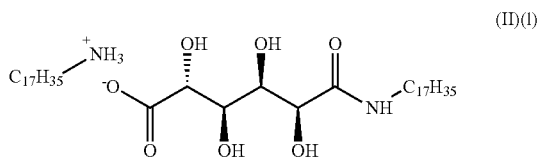

(II)(l)

In another embodiment, the compound of general formula (II) obtained in step (A) is octadecylammonium octadecylglucaramide (II)(m), also interchangeably referred as octadecylammonium (2R,3R,4R,5S)-6-(octadecylamino)-2,3,4, 5-tetrahydroxy-6-oxohexanoate, and is represented as shown hereinbelow

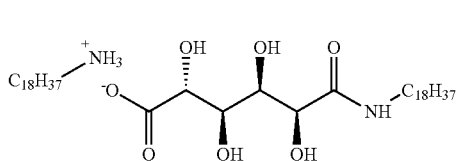

(II)(m)

In another embodiment, the compound of general formula (II) obtained in step (A) is hexenylammonium hexenylglucaramide (II)(n), also interchangeably referred as hexenylammonium (2R,3R,4R,5S)-6-(hexenylamino)-2,3,4,5-tetrahydroxy-6-oxohexanoate, and is represented as shown hereinbelow

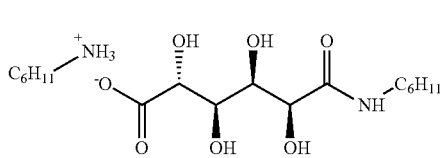

(II)(n)

In another embodiment, the compound of general formula (II) obtained in step (A) is heptenylammonium heptenylglucaramide (II)(o), also interchangeably referred as heptenylammonium (2R,3R,4R,5S)-6-(heptenylamino)-2,3,4,5-tetrahydroxy-6-oxohexanoate, and is represented as shown hereinbelow

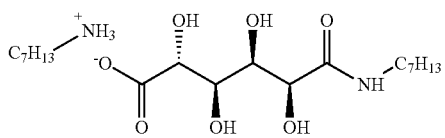

(II)(o)

In another embodiment, the compound of general formula (II) obtained in step (A) is octenylammonium octenylglucaramide (II)(p), also interchangeably referred as octenylammonium (2R,3R,4R,5S)-6-(octenylamino)-2,3,4,5-tetrahydroxy-6-oxohexanoate, and is represented as shown hereinbelow

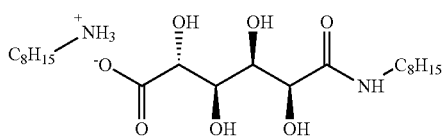

(II)(p)

In another embodiment, the compound of general formula (II) obtained in step (A) is nonenylammonium nonenylglucaramide (II)(q), also interchangeably referred as nonenylammonium (2R,3R,4R,5S)-6-(nonenylamino)-2,3,4,5-tetrahydroxy-6-oxohexanoate, and is represented as shown hereinbelow

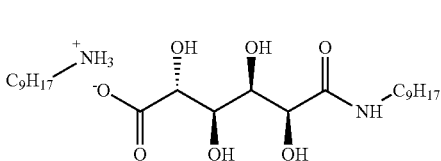

(II)(q)

In another embodiment, the compound of general formula (II) obtained in step (A) is decenylammonium decenylglucaramide (II)(r), also interchangeably referred as decenylammonium (2R,3R,4R,5S)-6-(decenylamino)-2,3,4,5-tetrahydroxy-6-oxohexanoate, and is represented as shown hereinbelow

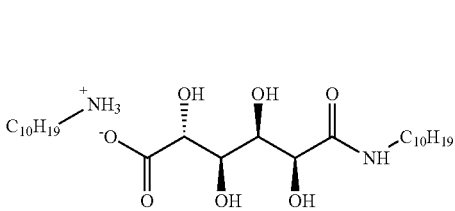

(II)(r)

In another embodiment, the compound of general formula (II) obtained in step (A) is undecenylammonium undecenylglucaramide (II)(s), also interchangeably referred as undecenylammonium (2R,3R,4R,5S)-6-(undecenylamino)-2,3,4,5-tetrahydroxy-6-oxohexanoate, and is represented as shown hereinbelow

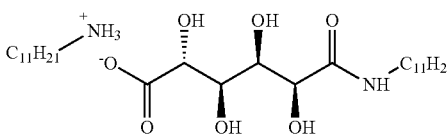

(II)(s)

In another embodiment, the compound of general formula (II) obtained in step (A) is dodecenylammonium dodecenylglucaramide (II)(t), also interchangeably referred as dodecenylammonium (2R,3R,4R,5S)-6-(dodecenylamino)-2,3,4,5-tetrahydroxy-6-oxohexanoate, and is represented as shown hereinbelow

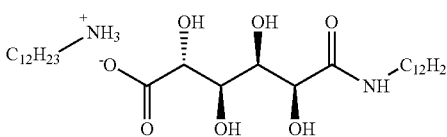

(II)(t)

In another embodiment, the compound of general formula (II) obtained in step (A) is tridecenylammonium tridecenylglucaramide (II)(u), also interchangeably referred as tridecenylammonium (2R,3R,4R,5S)-6-(tridecenylamino)-2,3,4,5-tetrahydroxy-6-oxohexanoate, and is represented as shown hereinbelow

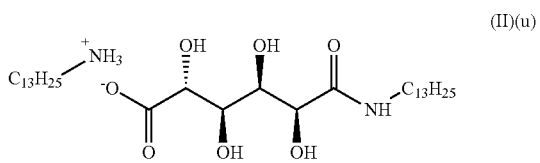

(II)(u)

In another embodiment, the compound of general formula (II) obtained in step (A) is tetradecenylammonium tetradecenylglucaramide (II)(v), also interchangeably referred as tetradecenylammonium (2R,3R,4R,5S)-6-(tetradecenylamino)-2,3,4,5-tetrahydroxy-6-oxohexanoate, and is represented as shown hereinbelow

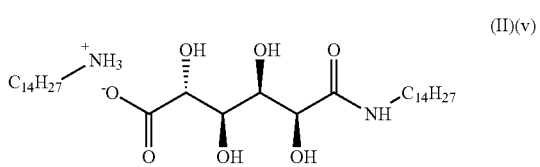

(II)(v)

In another embodiment, the compound of general formula (II) obtained in step (A) is pentadecenylammonium pentadecenylglucaramide (II)(w), also interchangeably referred as pentadecenylammonium (2R,3R,4R,5S)-6-(pentadecenylamino)-2,3,4,5-tetrahydroxy-6-oxohexanoate, and is represented as shown hereinbelow

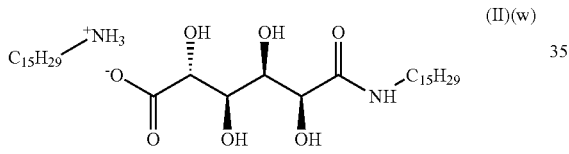

(II)(w)

In another embodiment, the compound of general formula (II) obtained in step (A) is hexadecenylammonium hexadecenylglucaramide (II)(x), also interchangeably referred as hexadecenylammonium (2R,3R,4R,5S)-6-(hexadecenylamino)-2,3,4,5-tetrahydroxy-6-oxohexanoate, and is represented as shown hereinbelow

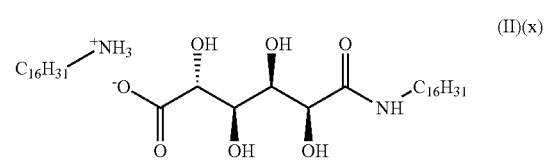

(II)(x)

In another embodiment, the compound of general formula (II) obtained in step (A) is heptadecenylammonium heptadecenylglucaramide (II)(y), also interchangeably referred as heptadecenylammonium (2R,3R,4R,5S)-6-(heptadecenylamino)-2,3,4,5-tetrahydroxy-6-oxohexanoate, and is represented as shown hereinbelow

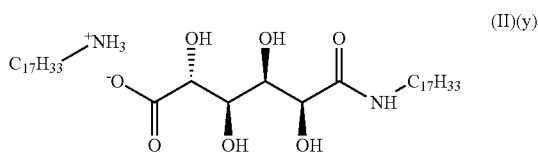

(II)(y)

In another embodiment, the compound of general formula (II) obtained in step (A) is octadecenylammonium octadecenylglucaramide (II)(z), also interchangeably referred as octadecenylammonium (2R,3R,4R,5S)-6-(octadecenylamino)-2,3,4,5-tetrahydroxy-6-oxohexanoate, and is represented as shown hereinbelow

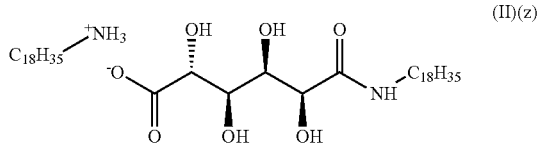

(II)(z)

In the step (B) of the process described hereinabove, the compound of general formula (II) obtained from step (A) is treated with an acid to obtain the compound of general formula (III)

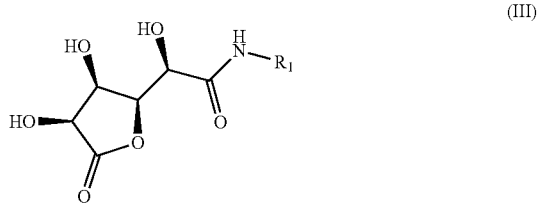

(III)

wherein, $R_1$ denotes unsubstituted, linear or branched, alkyl or alkenyl having 4 to 22 carbon atoms.

In order to obtain the desired product i.e. the compound of general formula (III), the compound of general formula (II) is dissolved in the at least one polar solvent prior to treating it with the acid. For the purpose of step (B) of the process, as described hereinabove, the term "compound of general formula (II)" refers to a mixture of the compound of general formula (II), as obtained in step (A), and the at least one polar solvent, as described hereinabove. However, unlike the step (A) where the at least one polar solvent was at least one alcohol solvent, the at least one polar solvent in step (B) is at least one ether solvent.

The at least one ether solvent generally include cyclic and acyclic ethers selected from the group consisting of tetrahydrofuran, 2-methyltetrahydrofuran, 1,4-dioxane, diethyl ether, diisopropyl ether, di-n-propyl ether, di-n-butyl ether, methyl-tert-butyl ether, diisobutyl ether, tetrahydropyran and dimethoxy-ethane. Preferably, the at least one ether solvent is selected from the group consisting of methyl tert-butyl ether, dioxane, tetrahydrofuran and tetrahydropyran. More preferably, it is selected from the group consisting of dioxane, tetrahydrofuran and tetrahydropyran. Most preferably, it is selected from the group consisting of tetrahydrofuran and tetrahydropyran.

For the purpose of dissolving the compound of general formula (II) in the at least one polar solvent prior to treating it with an acid, as described hereinabove, the amount of the at least one polar solvent is taken in excess of the compound of general formula (II). This results in a homogenous mixture of the compound of general formula (II) and the at least one polar solvent. However, the homogeneous mixture of the compound of general formula (II) and the at least one polar solvent may alternatively be a suspension or a solution depending on the amount and the temperature at which the said mixture is obtained. By the term "suspension", it is referred to the compound of general formula (II) suspended in the at least one polar solvent.

The present invention has a weight ratio between the at least one polar solvent and the compound of general formula (II) is in the range of ≥5:1 to ≤100:1. Preferably, the weight ratio is in the range of ≥6:1 to ≤100:1, or ≥6:1 to ≤95:1, or ≥6:1 to ≤90:1, or ≥6:1 to ≤85:1, or ≥6:1 to ≤80:1. More preferably, it is in the range of ≥7:1 to ≤80:1, or ≥7:1 to ≤75:1, or ≥7:1 to ≤70:1, or ≥7:1 to ≤65:1, or ≥7:1 to ≤60:1. Most preferably, it is in the range of ≥8:1 to ≤60:1, or ≥8.5:1 to 60:1, or ≥9:1 to ≤60:1, or ≥9.5:1 to ≤60:1. Particularly preferably, the weight ratio between the at least one polar solvent and the compound of general formula (II) is in the range of ≥10:1 to 60:1.

The compound of general formula (II), as described hereinabove, is now treated with an acid to obtain the desired product i.e. D-glucaro-6,3-lactone monoamide or the compound of general formula (III) in step (B) of the process. For the purpose of the present invention, the step (B) of the process described hereinabove is interchangeably referred as the treatment step. By the term "treated", it refers to mixing the compound of general formula (II), as described hereinabove, and the acid. By the term "mixing", it is referred to mechanical stirring using any suitable stirrer known to a person skilled in the art. The treatment step is not limited by the duration, type and rotational speed of the stirrer employed therein. These parameters are well-known to the person skilled in the art. However, typically the rotational speed in the range of ≥100 rpm to ≤1000 rpm for a period in the range of ≥0.1 h to ≤24 h is provided. Preferably, a temperature in the range of 10° C. to ≤60° C. is also maintained for a duration of ≥0.1 h to ≤10 h during mixing in the treatment step.

In an embodiment, the compound of general formula (III) obtained in the treatment step or step (B) of the process, as described hereinabove, exists in the form of a mixture comprising the compound of general formula (III), a compound of general formula (IV) and other impurities including any unreacted compounds and by-products. In order to selectively obtain the compound of general formula (III), it is essential that the compound of general formula (III) obtained as a mixture with other compounds is subjected to further purification. Accordingly, in an embodiment, the treatment step further includes at least one of heating, cooling, filtrating and washing. These additional steps further increase the yield and quality of the desired product. If mixing in the treatment step is followed by cooling, a temperature in the range of, such as but not limited to, ≥20° C. to ≤40° C. is provided. For the purpose of filtrating and washing, the at least one polar solvent, as described hereinabove, is employed and is taken in excess amounts. Preferably, the quantity of the at least one polar solvent employed for the purpose of filtrating and washing in step (B) is usually similar to that of the filtration and washing step or step (A2), as described hereinabove, i.e. the weight ratio between the at least one polar solvent and the compound of general formula (III), obtained by treating the compound of general formula (II) with the acid, is in the range of ≥1:15 to ≤15:1. A temperature in the range of ≥5° C. to ≤30° C. may also be provided for this purpose.

The compound of general formula (III) obtained in the process as described hereinabove is further subjected to drying, hereinafter interchangeably known as step (C) or drying step (C). The drying step (C) reduces the moisture and other impurities that might have formed or remained during the course of this process. The drying step (C), similar to the drying step or step (A3) described hereinabove, is performed under vacuum conditions to obtain the compound of general formula (II).

The drying step (C) may be performed by means of any suitable equipment known to a person skilled in the art which operate under vacuum conditions. These suitable equipments may be, such as but not limited to, rotary evaporators. The choice of a particular rotary evaporator should be made based on the desired conditions of temperature and pressure, as described hereinbelow.

For the purpose of the present invention, the drying step (C) is performed by evaporation which is carried out at reduced pressures, preferably under vacuum conditions. The vacuum pressure is maintained in the range of ≥0.1 mbar to ≤500 mbar. Preferably, the vacuum pressure is in the range of ≥0.1 mbar to ≤480 mbar. More preferably the vacuum pressure is in the range of ≥0.1 mbar to ≤460 mbar. Most preferably the vacuum pressure is in the range of ≥0.1 mbar to ≤450 mbar.

Typically, the temperature in the drying step (C) is in the range of ≥20° C. to ≤80° C. Preferably the temperature is in the range of ≥30° C. to ≤80° C. More preferably the temperature is in the range of ≥30° C. to ≤75° C. Most preferably the temperature is in the range of ≥40° C. to ≤75° C.

Typically, a duration in the range of ≥1 h to ≤55 h is provided during the drying step (C). Preferably the duration is in the range of ≥2 h to ≤45 h. More preferably the duration is in the range of ≥3 h to ≤35 h. Most preferably the duration is in the range of ≥4 h to ≤25 h.

The compound of general formula (III) obtained after the drying step (C) can be further purified by any purification techniques known to a person skilled in the art. The present process, as described hereinabove, is not limited to the choice and selection of the purification techniques. However, in an embodiment, the compound of general formula (III) obtained in step (C) is further dissolved in the at least one polar solvent, as described hereinabove for the purpose of step (B), cooled and filtered thereafter to finally obtain the desired product i.e. the compound of general formula (III) with improved yield and selectivity. The amounts of other impurities and/or compounds may be checked and verified by techniques known to the person skilled in the art, such as but not limited to, Nuclear Magnetic Resonance spectroscopy (NMR) technique.

The acid employed in the treatment step is selected from the group consisting of organic acid and inorganic acid. By the term "inorganic acid", it is referred to an acid derived from one or more inorganic compounds. The inorganic acid has an absence of carbon in its composition. Typical example of inorganic acids includes mineral acids. These mineral acids form hydrogen ions and conjugate base ions when dissolved in water. Preferably, such mineral acids may be selected from the group consisting of sulfuric acid, hydrochloric acid, nitric acid and phosphoric acid.

By the term "organic acid", it is referred to organic compounds possessing acidic properties. Typical examples of organic acid include organic compounds having carboxylic acid groups (—COOH) and sulfonic acid groups (—SO₃H). Other examples of organic acid include, such as but not limited to, acidic ion exchange resins. For the purpose of the present invention, the acid is preferably an organic acid. In an embodiment, the treatment step is carried out in the presence of an acidic ion exchange resin. The acidic ion exchange resin is a cation exchanger having acidic groups. Such acidic ion exchange resin is well known to a person skilled in the art. However, a cation exchange resin having acidic groups selected from the group consisting of, such as but not limited to, carboxylic acid and sulfonic acid is mostly preferred.

Strongly acidic cation exchangers are in particular ion exchange resins in the H⁺ form. Suitable acidic cation exchangers include, such as but not limited to, strongly acidic ion exchangers which are based on polystyrene and which comprise copolymers of styrene and a cross-linking agent such as divinylbenzene, with sulfonic acid groups in H⁺ form, ion exchanger groups functionalized with sulfonic acid groups (–SO₃H). These resins are often supplied as porous beads or granules, their high surface area:volume ratio maximising the rate of ion exchange and the total ion exchange capacity. They can be precisely engineered to have a particular porosity and surface chemistry, with these features facilitating selective and effective ion exchange.

The ion exchangers differ in the structure of their polymer backbones, and a distinction is made between gel-like and macroporous resins. The strongly acidic ion exchange resins are generally regenerated with hydrochloric acid and/or sulfuric acid.

For instance, Nafion® is a perfluorinated ion exchange material consisting of fluorocarbon base chains and perfluorinated side chains which comprise sulfonic acid groups. The resins are prepared by a copolymerization of perfluorinated, terminally unsaturated and sulfonyl-fluoride-functionalized ethoxylates with perfluoroethene. Nafion® belongs to the gel-like ion exchange resins.

In a particularly preferable embodiment, the strongly acidic cation exchanger is used in the H+ form, where the ion exchanger comprises a polymer backbone having sulfonic acid groups and is either gel-like or comprises macroporous resins.

For the purpose of the present invention, commercially available strongly acidic cation exchangers, such as but not limited to, Lewatit® by LANXESS, Purolite® by The Purolite Company, Dowex® by Dow Chemical Company, Amberlite® by Rohm and Haas Company and Amberlyst® by Rohm and Haas Company can be used as the acid for treating the compound of general formula (II) in the treatment step of the process, as described hereinabove.

The acidic cation exchange resin, as described hereinabove, has a concentration of active sites in the range of ≥1 eq/kg to ≤10 eq/kg. By the term "active sites", it is referred to the ion exchange sites available in the resin. Preferably, the concentration of active sites is in the range of ≥1 eq/kg to ≤9 eq/kg. More preferably, in the range of ≥1 eq/kg to ≤8 eq/kg. Most preferably, it is in the range of ≥1 eq/kg to ≤7 eq/kg, or ≥1 eq/kg to ≤6 eq/kg. In an embodiment, the concentration of active sites in the acidic cation exchange resin is in the range of ≥1 eq/kg to ≤5 eq/kg. In an embodiment, the acidic cation exchange resin may comprise ion exchange resin beads. The beads may have any suitable size i.e. diameter and suitable size distribution. Preferably, the beads have a mean diameter in the range of ≥20 µm to ≤1200 µm. More preferably, the mean diameter is in the range of ≥100 µm to ≤1100 µm, or ≥200 µm to ≤1000 µm. Most preferably, the mean diameter is in the range of ≥300 µm to ≤900 µm, or ≥400 µm to ≤800 µm, or ≥500 µm to ≤700 µm.

The acidic cation exchange resin may comprise porous resin beads. The porosity of the beads may be precisely engineered by controlling the conditions used in resin synthesis, such as the concentration of the cross-linking agent. The porosity of the beads can affect the surface area:volume ratio of the resin. The ion exchange resin may have any suitable surface area:volume ratio, however, it may be beneficial to maximise the surface area:volume ratio in order to maximize the rate of, and capacity for, cation exchange.

The surface area of the acidic cation exchange resin can be defined by the BET surface area value. By the term "BET surface area", it is hereby referred to the surface area measured using the Brunauer-Emmett-Teller theory. Any suitable equipment well known to the person skilled in the art can be employed for this purpose. Preferably, the BET surface area is in the range of ≥10 m²/g to ≤300 m²/g. More preferably, it is in the range of ≥10 m²/g to ≤250 m²/g, or ≥20 m²/g to ≤250 m²/g, or ≥20 m²/g to ≤200 m²/g. Most preferably, it is in the range of ≥30 m²/g to ≤200 m²/g, or ≥30 m²/g to ≤150 m²/g, or ≥40 m²/g to ≤150 m²/g, or ≥40 m²/g to ≤100 m²/g. In an embodiment, the acidic cation exchange resin has a BET surface area in the range of ≥40 m²/g to ≤75 m²/g.

The weight ratio between the acid and the compound of general formula (II), for the purpose of step (B) as described hereinabove, is in the range of ≥1:10 to ≤10:1. Preferably, the weight ratio is in the range of ≥1:10 to ≤10:1, or ≥1:10 to ≤10:1, or ≥1:10 to ≤10:1, or ≥1:10 to ≤10:1, or ≥1:10 to ≤10:1. More preferably, the weight ratio is in the range of ≥1:10 to ≤10:1, or ≥1:10 to ≤10:1, or ≥1:10 to ≤10:1, or ≥1:10 to ≤10:1, or ≥1:10 to ≤10:1. Most preferably, the weight ratio is in the range of ≥1:10 to ≤10:1, or ≥1:10 to ≤10:1, or ≥1:10 to ≤10:1, or ≥1:10 to ≤10:1, or ≥1:10 to ≤10:1. In an embodiment, the weight ratio between the acid and the compound of general formula (II) in the treatment step is in the range of The compound of general formula (III), as obtained in the process described hereinabove has an unsubstituted, linear or branched, alkyl or alkenyl having 4 to 22 carbon atoms, as denoted by R1. For the purpose of the present invention, the compound of general formula (III) may also be interchangeably referred as alkylglucaramidolactone or alkenylglucaramidolactone.

Preferably, in the compound of general formula (III), as described hereinabove, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (III) obtained in step (B) is hexylglucaramidolactone (III)(a), also interchangeably referred as (2R)-2-[(2S, 3R,4S)-3,4-dihydroxy5-oxo-tetrahydrofuran-2-yl]-2-hydroxy-N-hexyl-acetamide, and is represented as shown hereinbelow

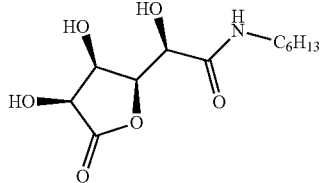
(III)(a)

In another embodiment, the compound of general formula (III) obtained in step (B) is heptylglucaramidolactone (III)(b), also interchangeably referred as (2R)-2-[(2S,3R,4S)-3,4-dihydroxy-5-oxo-tetrahydrofuran-2-yl]-2-hydroxy-N-heptyl-acetamide, and is represented as shown hereinbelow

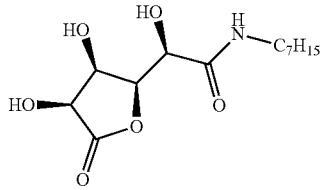
(III)(b)

In another embodiment, the compound of general formula (III) obtained in step (B) is octylglucaramidolactone (III)(c), also interchangeably referred as (2R)-2-[(2S,3R,4S)-3,4-dihydroxy-5-oxo-tetrahydrofuran-2-yl]-2-hydroxy-N-octyl-acetamide, and is represented as shown hereinbelow

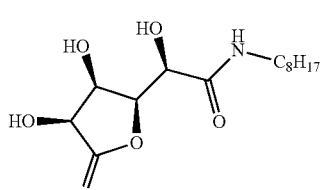
(III)(c)

In another embodiment, the compound of general formula (III) obtained in step (B) is nonylglucaramidolactone (III)(d), also interchangeably referred as (2R)-2-[(2S,3R,4S)-3,4-dihydroxy-5-oxo-tetrahydrofuran-2-yl]-2-hydroxy-N-nonyl-acetamide, and is represented as shown hereinbelow

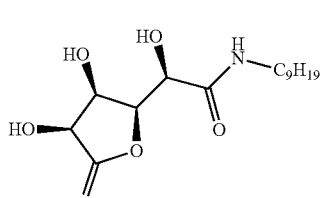
(III)(d)

In another embodiment, the compound of general formula (III) obtained in step (B) is decylglucaramidolactone (III)(e), also interchangeably referred as (2R)-2-[(2S,3R,4S)-3,4-dihydroxy-5-oxo-tetrahydrofuran-2-yl]-2-hydroxy-N-decyl-acetamide, and is represented as shown hereinbelow

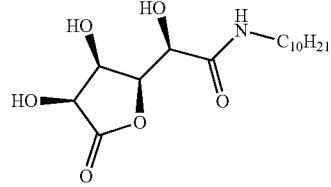
(III)(e)

In another embodiment, the compound of general formula (III) obtained in step (B) is undecylglucaramidolactone (III)(f), also interchangeably referred as (2R)-2-[(2S,3R,4S)-3,4-dihydroxy-5-oxo-tetrahydrofuran-2-yl]-2-hydroxy-N-undecyl-acetamide, and is represented as shown hereinbelow

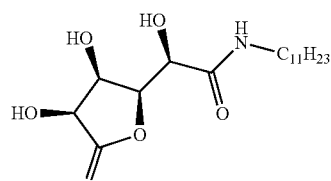
(III)(f)

In another embodiment, the compound of general formula (III) obtained in step (B) is dodecylglucaramidolactone (III)(g), also interchangeably referred as (2R)-2-[(2S,3R,4S)-3,4-dihydroxy-5-oxo-tetrahydrofuran-2-yl]-N-dodecyl-2-hydroxy-acetamide, and is represented as shown hereinbelow

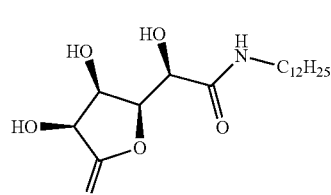
(III)(g)

In another embodiment, the compound of general formula (III) obtained in step (B) is tridecylglucaramidolactone (III)(h), also interchangeably referred as (2R)-2-[(2S,3R,4S)-3,4-dihydroxy-5-oxo-tetrahydrofuran-2-yl]-2-hydroxy-N-tridecyl-acetamide, and is represented as shown hereinbelow

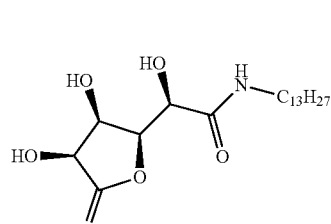
(III)(h)

In another embodiment, the compound of general formula (III) obtained in step (B) is tetradecylglucaramidolactone (III)(i), also interchangeably referred as (2R)-2-[(2S,3R,4S)-3,4-dihydroxy-5-oxo-tetrahydrofuran-2-yl]-2-hydroxy-N-tetradecyl-acetamide, and is represented as shown hereinbelow

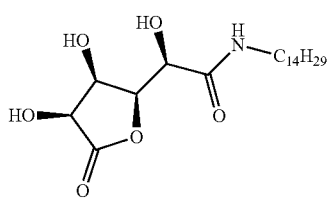
(III)(i)

In another embodiment, the compound of general formula (III) obtained in step (B) is pentadecylglucaramidolactone (III)(j), also interchangeably referred as (2R)-2-[(2S,3R,4S)-3,4-dihydroxy-5-oxo-tetrahydrofuran-2-yl]-2-hydroxy-N-pentadecyl-acetamide, and is represented as shown hereinbelow

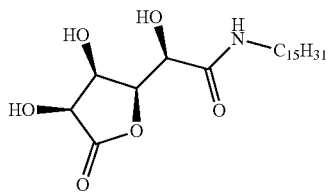
(III)(j)

In another embodiment, the compound of general formula (111) obtained in step (B) is hexadecylglucaramidolactone (111)(k), also interchangeably referred as (2R)-2-[(2S,3R,4S)-3,4-dihydroxy-5-oxo-tetrahydrofuran-2-yl]-N-hexadecyl-2-hydroxy-acetamide, and is represented as shown hereinbelow

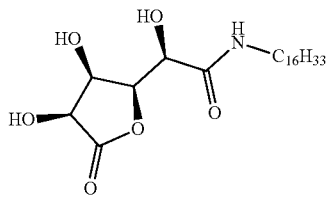
(III)(k)

In another embodiment, the compound of general formula (111) obtained in step (B) is heptadecylglucaramidolactone (111)(1), also interchangeably referred as (2R)-2-[(2S,3R,4S)-3,4-dihydroxy-5-oxo-tetrahydrofuran-2-yl]-N-heptadecyl-2-hydroxy-acetamide, and is represented as shown hereinbelow

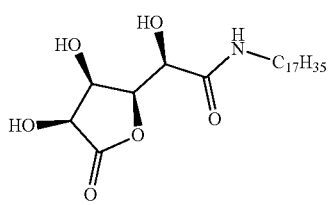
(III)(l)

In another embodiment, the compound of general formula (111) obtained in step (B) is octadecyl-glucaramidolactone (111)(m) R2R)-2-[(2S,3R,4S)-3,4-dihydroxy-5-oxo-tetrahydrofuran-2-yl]-2-hydroxy-N-octadecyl-acetamide, and is represented as shown hereinbelow

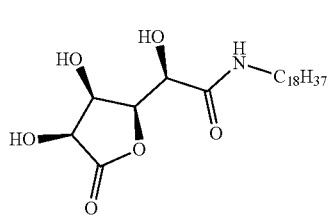
(III)(m)

In another embodiment, the compound of general formula (111) obtained in step (B) is hexenylglucaramidolactone (III)(n), also interchangeably referred as (2R)-2-[(2S,3R,4S)-3,4-dihydroxy-5-oxo-tetrahydrofuran-2-yl]-N-hexenyl-2-hydroxy-acetamide, and is represented as shown hereinbelow

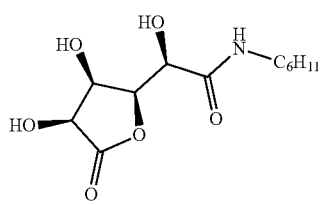
(III)(n)

In another embodiment, the compound of general formula (III) obtained in step (B) is heptenylglucaramidolactone (III)(o), also interchangeably referred as (2R)-2-[(2S,3R,4S)-3,4-dihydroxy-5-oxo-tetrahydrofuran-2-yl]-N-heptenyl-2-hydroxy-acetamide, and is represented as shown hereinbelow

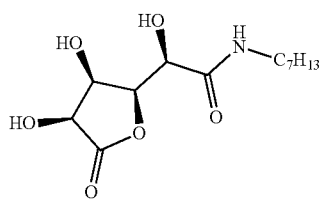
(III)(o)

In another embodiment, the compound of general formula (III) obtained in step (B) is octenylglucaramidolactone (III)(p), also interchangeably referred as (2R)-2-[(2S,3R,4S)-3,4-dihydroxy-5-oxo-tetrahydrofuran-2-yl]-2-hydroxy-N-octenyl-acetamide, and is represented as shown hereinbelow

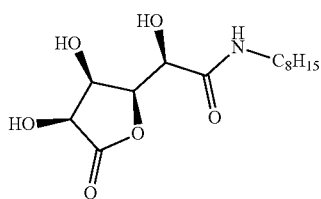
(III)(p)

In another embodiment, the compound of general formula (III) obtained in step (B) is nonenylglucaramidolactone (III)(q), also interchangeably referred as (2R)-2-[(2S,3R,4S)-3,4-dihydroxy-5-oxo-tetrahydrofuran-2-yl]-2-hydroxy-N-nonenyl-acetamide, and is represented as shown hereinbelow

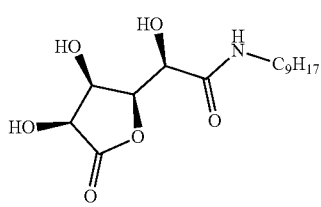
(III)(q)

In another embodiment, the compound of general formula (III) obtained in step (B) is decenylglucaramidolactone (III)(r), also interchangeably referred as (2R)-2-[(2S,3R,4S)-3,4-dihydroxy-5-oxo-tetrahydrofuran-2-yl]-2-hydroxy-N-decenyl-acetamide, and is represented as shown hereinbelow

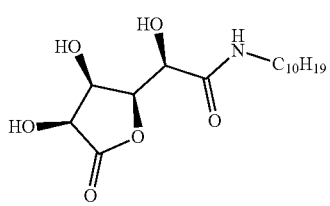
(III)(r)

In another embodiment, the compound of general formula (III) obtained in step (B) is undecenyl-glucaramidolactone (III)(s), also interchangeably referred as (2R)-2-[(2S,3R,4S)-3,4-dihydroxy-5-oxo-tetrahydrofuran-2-yl]-2-hydroxy-N-undecenyl-acetamide, and is represented as shown hereinbelow

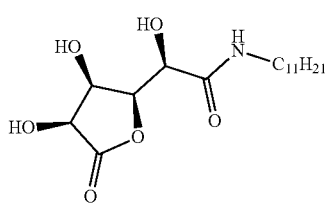
(III)(s)

In another embodiment, the compound of general formula (III) obtained in step (B) is dodecenyl-glucaramidolactone (III)(t), also interchangeably referred as (2R)-2-[(2S,3R,4S)-3,4-dihydroxy-5-oxo-tetrahydrofuran-2-yl]-N-dodecenyl-2-hydroxy-acetamide, and is represented as shown hereinbelow

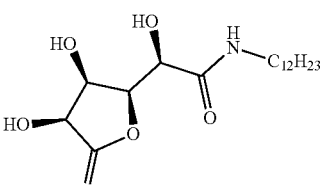
(III)(t)

In another embodiment, the compound of general formula (III) obtained in step (B) is tridecenyl-glucaramidolactone (III)(u), also interchangeably referred as (2R)-2-[(2S,3R,4S)-3,4-dihydroxy-5-oxo-tetrahydrofuran-2-yl]-2-hydroxy-N-tridecenyl-acetamide, and is represented as shown hereinbelow

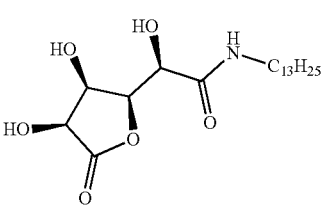
(III)(u)

In another embodiment, the compound of general formula (III) obtained in step (B) is tetradecenylglucaramidolactone (III)(v), also interchangeably referred as (2R)-2-[(2S,3R,4S)-3,4-dihydroxy-5-oxo-tetrahydrofuran-2-yl]-2-hydroxy-N-tetradecenyl-acetamide, and is represented as shown hereinbelow

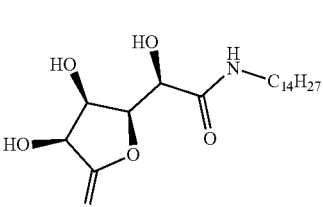
(III)(v)

In another embodiment, the compound of general formula (111) obtained in step (B) is pentadecenylglucaramidolactone (III)(w), also interchangeably referred as (2R)-2-[(2S,3R,4S)-3,4-dihydroxy-5-oxo-tetrahydrofuran-2-yl]-2-hydroxy-N-pentadecenyl-acetamide, and is represented as shown hereinbelow

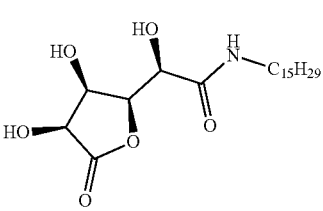
(III)(w)

In another embodiment, the compound of general formula (III) obtained in step (B) is hexadecenylglucaramidolactone (III)(x), also interchangeably referred as (2R)-2-[(2S,3R,4S)-3,4-dihydroxy-5-oxo-tetrahydrofuran-2-yl]-N-hexadecenyl-2-hydroxy-acetamide, and is represented as shown hereinbelow

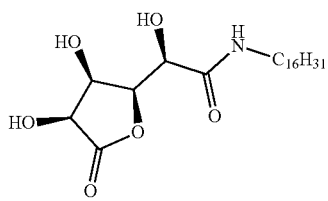
(III)(x)

In another embodiment, the compound of general formula (III) obtained in step (B) is heptade-cenylglucaramidolactone (III)(y), also interchangeably referred as (2R)-2-[(2S,3R,4S)-3,4-dihydroxy-5-oxo-tetrahydrofuran-2-yl]-N-heptadecenyl-2-hydroxy-acetamide, and is represented as shown hereinbelow

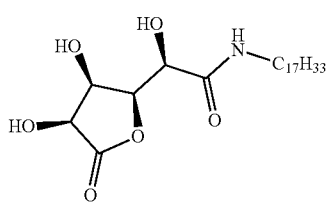
(III)(y)

In another embodiment, the compound of general formula (III) obtained in step (B) is octadecenyl-glucaramidolactone (III)(z), also interchangeably referred as (2R)-2-[(2S,3R,4S)-3,4-dihydroxy-5-oxo-tetrahydrofuran-2-yl]-2-hydroxy-N-octadecenyl-acetamide, and is represented as shown hereinbelow

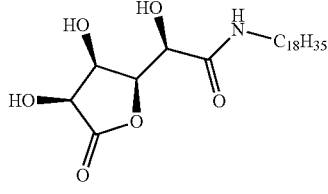
(III)(z)

In addition to the compound of general formula (III), as described hereinabove in step (B) of the process, the compound of general formula (IV) may also be obtained. Accordingly, in an embodiment the desired product obtained in step (B) of the process described hereinabove is the mixture comprising the compound of general formula (III), a compound of general formula (IV) and other impurities including any unreacted compounds and by-products. Although, it is particularly preferable to obtain the compound of general formula (III) without any impurities and/or unwanted by-products such as the compound of general formula (IV), it is difficult to completely avoid the formation of these compounds and therefore, the compound of general formula (III) obtained in step (B) may be a mixture of other compounds and/or impurities, but these being present in small quantities.

The compound of general formula (IV), hereinafter interchangeably also referred as alkylamidoglucaric acid, can be represented as shown hereinbelow

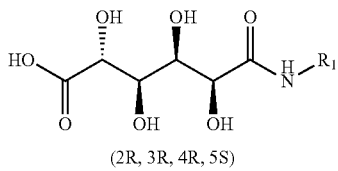
(IV)

(2R, 3R, 4R, 5S)

wherein, $R_1$ denotes unsubstituted, linear or branched, alkyl or alkenyl having 4 to 22 carbon atoms.

Preferably, in the compound of general formula (IV), as described hereinabove, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (IV) obtained in step (B) is hexylamidoglucaric acid (IV)(a), also interchangeably referred as (2R,3R,4R,5S)-6-(hexylamino)-2,3,4,5-tetrahydroxy-6-oxo-hexanoic acid, and is represented as shown hereinbelow

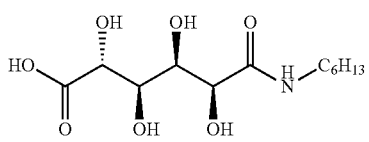
(IV)(a)

In another embodiment, the compound of general formula (IV) obtained in step (B) is heptylamidoglucaric acid (IV)(b), also interchangeably referred as (2R,3R,4R,5S)-6-(heptylamino)-2,3,4,5-tetrahydroxy-6-oxo-hexanoic acid, and is represented as shown hereinbelow

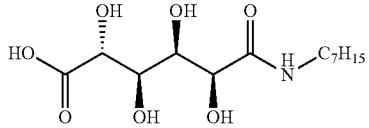
(IV)(b)

In another embodiment, the compound of general formula (IV) obtained in step (B) is octylamidoglucaric acid (IV)(c), also interchangeably referred as (2R,3R,4R,5S)-6-(octylamino)-2,3,4,5-tetrahydroxy-6-oxo-hexanoic acid, and is represented as shown hereinbelow

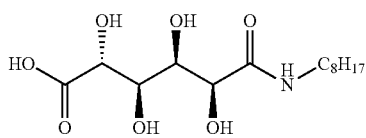
(IV)(c)

In another embodiment, the compound of general formula (IV) obtained in step (B) is nonylamidoglucaric acid (IV)(d), also interchangeably referred as (2R,3R,4R,5S)-6-(nonylamino)-2,3,4,5-tetrahydroxy-6-oxo-hexanoic acid, and is represented as shown hereinbelow

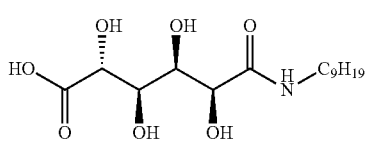
(IV)(d)

In another embodiment, the compound of general formula (IV) obtained in step (B) is decylamidoglucaric acid (III)(e), also interchangeably referred as (2R,3R,4R,5S)-6-(decylamino)-2,3,4,5-tetrahydroxy-6-oxo-hexanoic acid, and is represented as shown hereinbelow

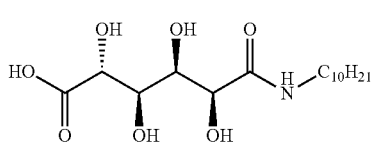
(IV)(e)

In another embodiment, the compound of general formula (IV) obtained in step (B) is undecylamidoglucaric acid (IV)(f), also interchangeably referred as (2R,3R,4R,5S)-6-(undecylamino)-2,3,4,5-tetrahydroxy-6-oxo-hexanoic acid, and is represented as shown hereinbelow

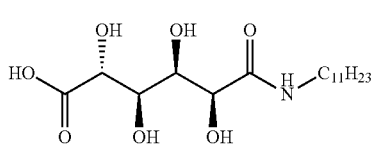
(IV)(f)

In another embodiment, the compound of general formula (IV) obtained in step (B) is dodecylamidoglucaric acid (IV)(g), also interchangeably referred as (2R,3R,4R,5S)-6-(dodecylamino)-2,3,4,5-tetrahydroxy-6-oxo-hexanoic acid, and is represented as shown hereinbelow

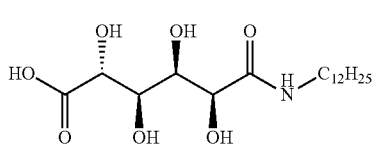
(IV)(g)

In another embodiment, the compound of general formula (IV) obtained in step (B) is tridecylamidoglucaric acid (IV)(h), also interchangeably referred as (2R,3R,4R,5S)-6-(tridecylamino)2,3,4,5-tetrahydroxy-6-oxo--hexanoic acid, and is represented as shown hereinbelow

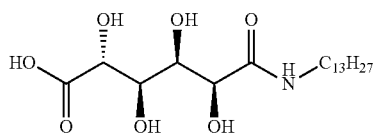
(IV)(h)

In another embodiment, the compound of general formula (IV) obtained in step (B) is tetradecylamidoglucaric acid (IV)(i), also interchangeably referred as (2R,3R,4R,5S)-6-(tetradecylamino)-2,3,4,5-tetrahydroxy-6-oxo-hexanoic acid, and is represented as shown hereinbelow

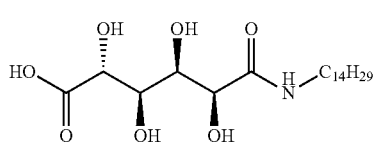
(IV)(i)

In another embodiment, the compound of general formula (IV) obtained in step (B) is pentadecylamidoglucaric acid (IV)(j), also interchangeably referred as (2R,3R,4R,5S)-6-(pentadecylamino)2,3,4,5-tetrahydroxy-6-oxo-hexanoic acid, and is represented as shown hereinbelow

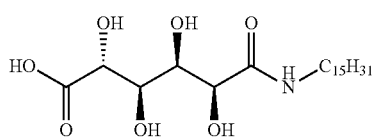
(IV)(j)

In another embodiment, the compound of general formula (IV) obtained in step (B) is hexadecyl-amidoglucaric acid (IV)(k), also interchangeably referred as (2R,3R,4R,5S)-6-(hexadecylamino)-2,3,4,5-tetrahydroxy-6-oxo-hexanoic acid, and is represented as shown hereinbelow

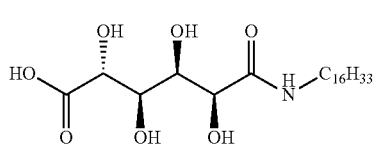
(IV)(k)

In another embodiment, the compound of general formula (IV) obtained in step (B) is heptadecyl-amidoglucaric acid (IV)(l), also interchangeably referred as (2R,3R,4R,5S)-6-(heptadecylamino)-2,3,4,5-tetrahydroxy-6-oxo-hexanoic acid, and is represented as shown hereinbelow

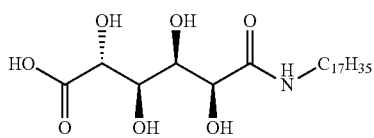
(IV)(l)

In another embodiment, the compound of general formula (IV) obtained in step (B) is octadecyl-amidoglucaric acid (IV)(m), also interchangeably referred as (2R,3R,4R,5S)-6-(octadecylamino)-2,3,4,5-tetrahydroxy-6-oxo-hexanoic acid, and is represented as shown hereinbelow

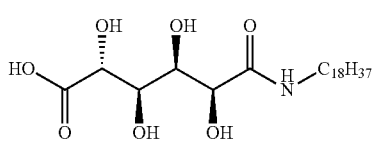
(IV)(m)

In another embodiment, the compound of general formula (IV) obtained in step (B) is hexenylami-doglucaric acid (IV)(n), also interchangeably referred as (2R,3R,4R,5S)-6-(hexenylamino)-2,3,4,5-tetrahydroxy-6-oxo-hexanoic acid, and is represented as shown hereinbelow

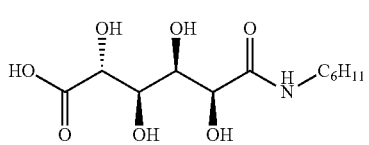
(IV)(n)

In another embodiment, the compound of general formula (IV) obtained in step (B) is heptenyl-amidoglucaric acid (IV)(o), also interchangeably referred as (2R,3R,4R,5S)-6-(heptenylamino)-2,3,4,5-tetrahydroxy-6-oxo-hexanoic acid, and is represented as shown hereinbelow

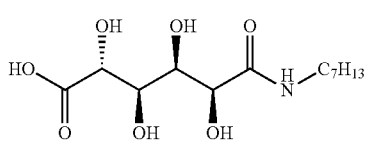
(IV)(o)

In another embodiment, the compound of general formula (IV) obtained in step (B) is octenylamidoglucaric acid (IV)(p), also interchangeably referred as (2R,3R,4R,5S)-6-(octenylamino)-2,3,4,5-tetrahydroxy-6-oxo-hexanoic acid, and is represented as shown hereinbelow

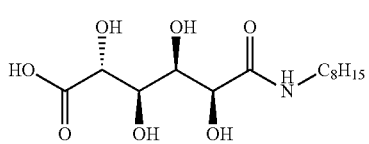
(IV)(p)

In another embodiment, the compound of general formula (IV) obtained in step (B) is nonenyl-amidoglucaric acid (IV)(q), also interchangeably referred as (2R,3R,4R,5S)-6-(nonenylamino)-2,3,4,5-tetrahydroxy-6-oxo-hexanoic acid, and is represented as shown hereinbelow

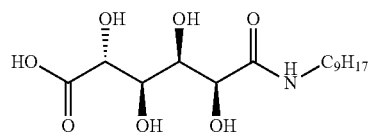
(IV)(q)

In another embodiment, the compound of general formula (IV) obtained in step (B) is decenylami-doglucaric acid (III)(r), also interchangeably referred as (2R,3R,4R,5S)-6-(decenylamino)-2,3,4,5-tetrahydroxy-6-oxo-hexanoic acid, and is represented as shown hereinbelow

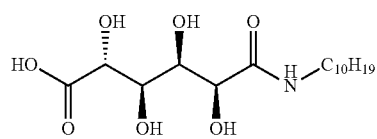
(IV)(r)

In another embodiment, the compound of general formula (IV) obtained in step (B) is undecenyl-amidoglucaric acid (IV)(s), also interchangeably referred as (2R,3R,4R,5S)-6-(undecenylamino)-2,3,4,5-tetrahydroxy-6-oxo-hexanoic acid, and is represented as shown hereinbelow

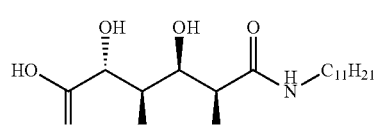
(IV)(s)

In another embodiment, the compound of general formula (IV) obtained in step (B) is dodecenyl-amidoglucaric acid (IV)(t), also interchangeably referred as (2R,3R,4R,5S)-6-(dodecenylamino)-2,3,4,5-tetrahydroxy-6-oxo-hexanoic acid, and is represented as shown hereinbelow

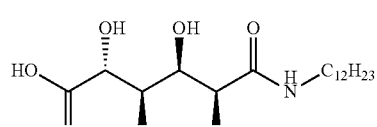
(IV)(t)

In another embodiment, the compound of general formula (IV) obtained in step (B) is tridecenyl-amidoglucaric acid (IV)(u), also interchangeably referred as (2R,3R,4R,5S)-6-(tridecenylamino)-2,3,4,5-tetrahydroxy-6-oxo-hexanoic acid, and is represented as shown hereinbelow

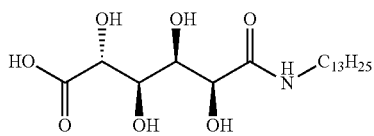
(IV)(u)

In another embodiment, the compound of general formula (IV) obtained in step (B) is tetradecenylamidoglucaric acid (IV)(v), also interchangeably referred as (2R,3R,4R,5S)-6-(tetradecenyl-amino)-2,3,4,5-tetrahydroxy-6-oxo-hexanoic acid, and is represented as shown hereinbelow

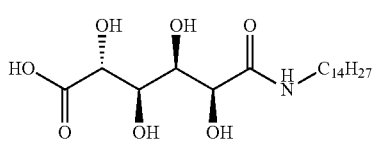
(IV)(v)

In another embodiment, the compound of general formula (IV) obtained in step (B) is pentadecenylamidoglucaric acid (IV)(w), also interchangeably referred as (2R,3R,4R,5S)-6-(pentadecenylamino)-2,3,4,5-tetrahydroxy-6-oxo-hexanoic acid, and is represented as shown hereinbelow

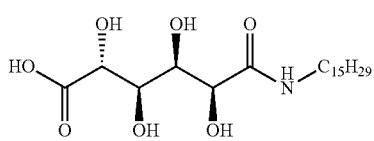
(IV)(w)

In another embodiment, the compound of general formula (IV) obtained in step (B) is hexadecenylamidoglucaric acid (IV)(x), also interchangeably referred as (2R,3R,4R,5S)-6-(hexadecenylamino)-2,3,4,5-tetrahydroxy-6-oxo-hexanoic acid, and is represented as shown hereinbelow

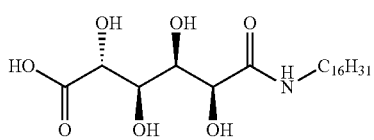
(IV)(x)

In another embodiment, the compound of general formula (IV) obtained in step (B) is heptadecenylamidoglucaric acid (IV)(y), also interchangeably referred as (2R,3R,4R,5S)-6-(heptadecenylamino)-2,3,4,5-tetrahydroxy-6-oxo-hexanoic acid, and is represented as shown hereinbelow

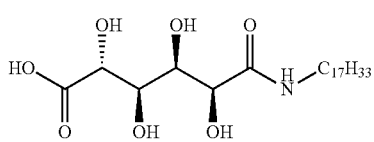
(IV)(y)

In another embodiment, the compound of general formula (IV) obtained in step (B) is octadecenylamidoglucaric acid (IV)(z), also interchangeably referred as (2R,3R,4R,5S)-6-(octadecenylamino)-2,3,4,5-tetrahydroxy-6-oxo-hexanoic acid, and is represented as shown hereinbelow

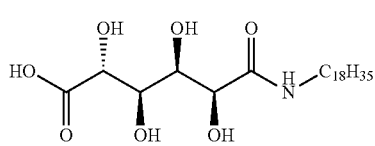
(IV)(z)

For the purpose of the present invention, the process as described hereinabove has the temporal sequence of the steps as (A1)→(A2)→(A4)→(B)→(C). Alternatively, the process may have the temporal sequence of the steps as (A1)→(A2)→(A4)→(B).

In another embodiment of the present invention, the process has the temporal sequence of the steps as (A1)→(A2)→(A3)→(A4)→(B)→(C). Alternatively, the process may have the temporal sequence of the steps as (A1)→(A2)→(A3)→(A4)→(B).

The novel synthesis route, as described hereinabove, has several advantages over the current state of the art. The current state of the art available, such as but not limited to the one described by, Zenner et.al. [Institute of Organic Chemistry at the University of Rostock, Mar. 12, 1956 ] reports to have obtained diamide of D-glucaric acid at room temperature and with one molar equivalent of the amine used therein. However, surprisingly the novel synthesis route or the present invention process even at low temperature conditions, such as those described hereinabove, results in the formation of the desired compound with maximized selectivity and yield while that of the by-products and/or unwanted impurities, such as but not limited to, the compound of general formula (IV) is suppressed. Another advantage of the present invention process includes economical operation of the process due to low process conditions especially temperature and pressure as well as the use of easily available raw materials such as but not limited to the at least one polar solvent, the salt of D-glucaro-6,3-lactone and the acid, as described hereinabove. Moreover, the ease of scaling the process conditions of the present invention enables it to meet the huge industrial requirements.

Another aspect of the present invention relates to the compounds of general formula (II)

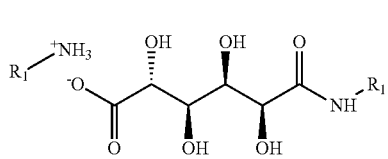
(II)

wherein, $R_1$ denotes unsubstituted, linear or branched, alkyl or alkenyl having 4 to 22 carbon atoms.

The compound of general formula (II), as described hereinabove, is also interchangeably referred as alkylammonium alkylglucaramide or alkenylammonium alkenylglucaramide, having unsubstituted, linear or branched, alkyl or alkenyl having 4 to 22 carbon atoms, as denoted by $R_1$. Preferably, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (II) is hexylammonium hexylglucaramide (II)(a), also interchangeably referred as hexylammonium (2R,3R,4R,5S)-6-(hexylamino)-2,3,4,5-tetrahydroxy-6-oxohexanoate, and is represented as shown hereinbelow

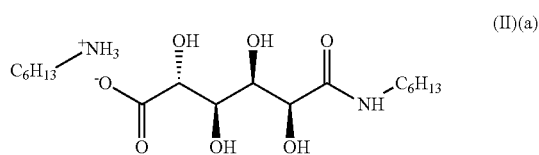

In another embodiment, the compound of general formula (II) is heptylammonium heptylglucaramide (II)(b), also interchangeably referred as heptylammonium (2R,3R,4R,5S)-6-(heptylamino)-2,3,4,5-tetrahydroxy-6-oxohexanoate, and is represented as shown hereinbelow

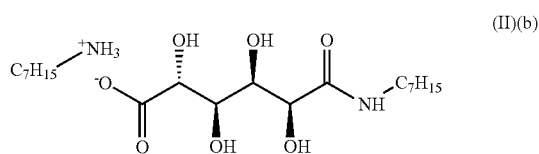

In another embodiment, the compound of general formula (II) is octylammonium octylglucaramide (II)(c), also interchangeably referred as octylammonium (2R,3R,4R,5S)-6-(octylamino)-2,3,4,5-tetrahydroxy-6-oxohexanoate, and is represented as shown hereinbelow

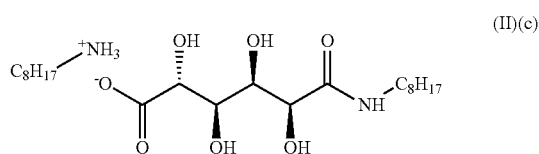

In another embodiment, the compound of general formula (II) is nonylammonium nonylglucaramide (II)(d), also interchangeably referred as nonylammonium (2R,3R,4R,5S)-6-(nonylamino)-2,3,4,5-tetrahydroxy-6-oxohexanoate, and is represented as shown hereinbelow

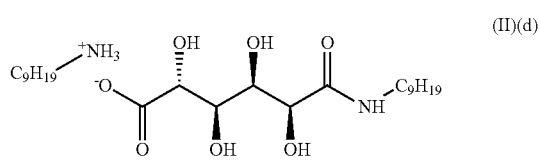

In another embodiment, the compound of general formula (II) is decylammonium decylglucaramide (II)(e), also interchangeably referred as decylammonium (2R,3R,4R,5S)-6-(decylamino)-2,3,4,5-tetrahydroxy-6-oxohexanoate, and is represented as shown hereinbelow

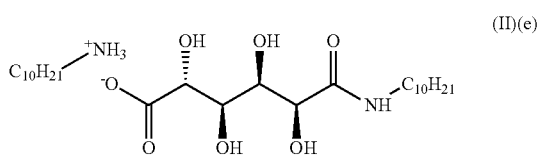

In another embodiment, the compound of general formula (II) is undecylammonium undecylglucaramide (II)(f), also interchangeably referred as undecylammonium (2R,3R,4R,5S)-6-(undecylamino)-2,3,4,5-tetrahydroxy-6-oxohexanoate, and is represented as shown hereinbelow

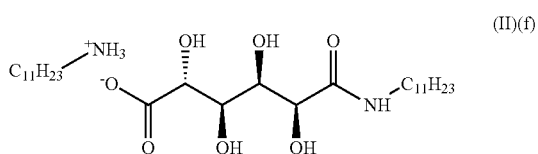

In another embodiment, the compound of general formula (II) is dodecylammonium dodecylglucaramide (II)(g), also interchangeably referred as dodecylammonium (2R,3R,4R,5S)-6-(dodecyl-amino)-2,3,4,5-tetrahydroxy-6-oxohexanoate, and is represented as shown hereinbelow

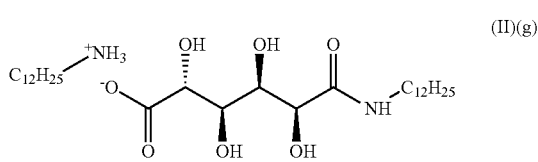

In another embodiment, the compound of general formula (II) is tridecylammonium tridecylglucaramide (II)(h), also interchangeably referred as tridecylammonium (2R,3R,4R,5S)-6-(tridecylamino)-2,3,4,5-tetrahydroxy-6-oxohexanoate, and is represented as shown hereinbelow

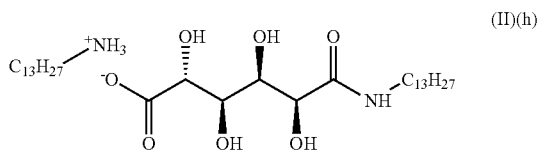

In another embodiment, the compound of general formula (II) is tetradecylammonium tetradecylglucaramide (II)(i), also interchangeably referred as tetradecylammonium (2R,3R,4R,5S)-6-(tetradecylamino)-2,3,4,5-tetrahydroxy-6-oxohexanoate, and is represented as shown hereinbelow

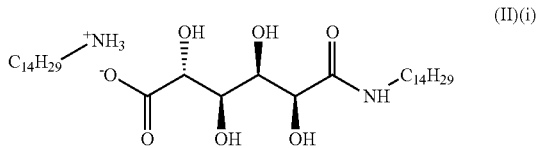

(II)(i)

In another embodiment, the compound of general formula (II) is pentadecylammonium pentadecylglucaramide (II)(j), also interchangeably referred as pentadecylammonium (2R,3R,4R,5S)-6-(pentadecylamino)-2,3,4,5-tetrahydroxy-6-oxohexanoate, and is represented as shown hereinbelow

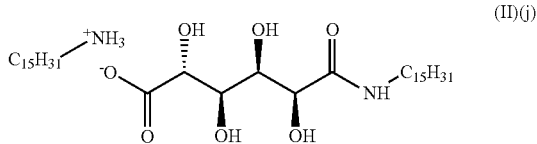

(II)(j)

In another embodiment, the compound of general formula (II) is hexadecylammonium hexadecylglucaramide (II)(k), also interchangeably referred as hexadecylammonium (2R,3R,4R,5S)-6-(hexadecylamino)-2,3,4,5-tetrahydroxy-6-oxohexanoate, and is represented as shown hereinbelow

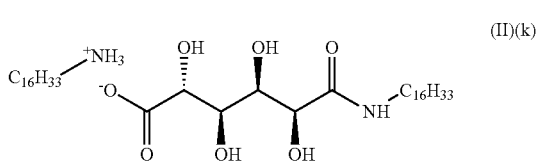

(II)(k)

In another embodiment, the compound of general formula (II) is heptadecylammonium heptadecylglucaramide (II)(l), also interchangeably referred as heptadecylammonium (2R,3R,4R,5S)-6-(heptadecylamino)-2,3,4,5-tetrahydroxy-6-oxohexanoate, and is represented as shown hereinbelow

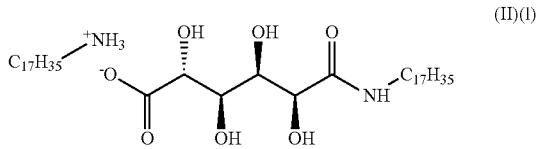

(II)(l)

In another embodiment, the compound of general formula (II) is octadecylammonium octadecylglucaramide (II)(m), also interchangeably referred as octadecylammonium (2R,3R,4R,5S)-6-(octadecylamino)-2,3,4,5-tetrahydroxy-6-oxohexanoate, and is represented as shown hereinbelow

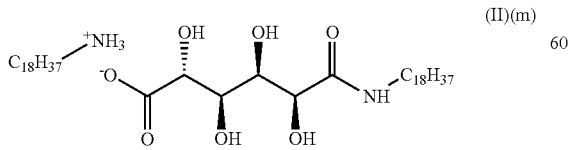

(II)(m)

In another embodiment, the compound of general formula (II) is hexenylammonium hexenylglucaramide (II)(n), also interchangeably referred as hexenylammonium (2R,3R,4R,5S)-6-(hexenylamino)-2,3,4,5-tetrahydroxy-6-oxohexanoate, and is represented as shown hereinbelow

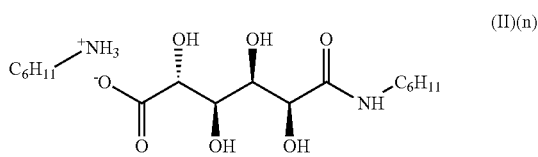

(II)(n)

In another embodiment, the compound of general formula (II) is heptenylammonium heptenylglucaramide (II)(o), also interchangeably referred as heptenylammonium (2R,3R,4R,5S)-6-(heptenylamino)-2,3,4,5-tetrahydroxy-6-oxohexanoate, and is represented as shown hereinbelow

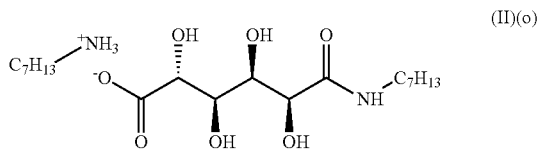

(II)(o)

In another embodiment, the compound of general formula (II) is octenylammonium octenylglucaramide (II)(p), also interchangeably referred as octenylammonium (2R,3R,4R,5S)-6-(octenylamino)-2,3,4,5-tetrahydroxy-6-oxohexanoate, and is represented as shown hereinbelow

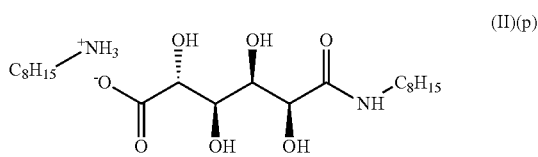

(II)(p)

In another embodiment, the compound of general formula (II) is nonenylammonium nonenylglucaramide (II)(q), also interchangeably referred as nonenylammonium (2R,3R,4R,5S)-6-(nonenylamino)-2,3,4,5-tetrahydroxy-6-oxohexanoate, and is represented as shown hereinbelow

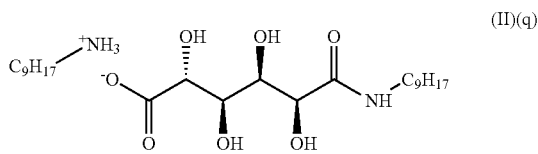

(II)(q)

In another embodiment, the compound of general formula (II) is decenylammonium decenylglucaramide (II)(r), also interchangeably referred as decenylammonium (2R,3R,4R,5S)-6-(decenylamino)-2,3,4,5-tetrahydroxy-6-oxohexanoate, and is represented as shown hereinbelow

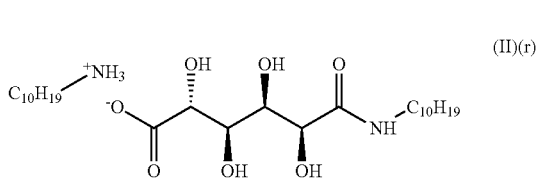
(II)(r)

In another embodiment, the compound of general formula (II) is undecenylammonium undecenylglucaramide (II)(s), also interchangeably referred as undecenylammonium (2R,3R,4R,5S)-6-(undecenylamino)-2,3,4,5-tetrahydroxy-6-oxohexanoate, and is represented as shown hereinbelow

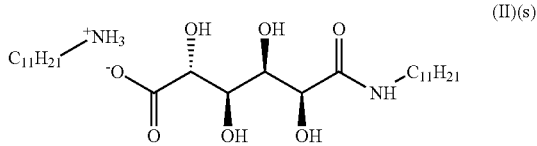
(II)(s)

In another embodiment, the compound of general formula (II) is dodecenylammonium dodecenylglucaramide (II)(t), also interchangeably referred as dodecenylammonium (2R,3R,4R,5S)-6-(dodecenylamino)-2,3,4,5-tetrahydroxy-6-oxohexanoate, and is represented as shown hereinbelow

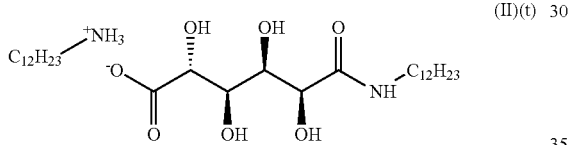
(II)(t)

In another embodiment, the compound of general formula (II) is tridecenylammonium tridecenylglucaramide (II)(u), also interchangeably referred as tridecenylammonium (2R,3R,4R,5S)-6-(tridecenylamino)-2,3,4,5-tetrahydroxy-6-oxohexanoate, and is represented as shown hereinbelow

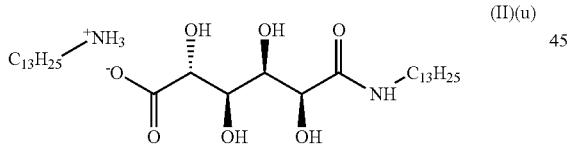
(II)(u)

In another embodiment, the compound of general formula (II) is tetradecenylammonium tetradecenylglucaramide (II)(v), also interchangeably referred as tetradecenylammonium (2R,3R,4R,5S)-6-(tetradecenylamino)-2,3,4,5-tetrahydroxy-6-oxohexanoate, and is represented as shown hereinbelow

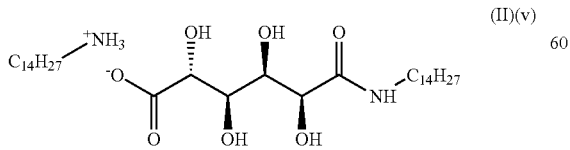
(II)(v)

In another embodiment, the compound of general formula (II) is pentadecenylammonium pentadecenylglucaramide (II)(w), also interchangeably referred as pentadecenylammonium (2R,3R,4R,5S)-6-(pentadecenylamino)-2,3,4,5-tetrahydroxy-6-oxohexanoate, and is represented as shown hereinbelow

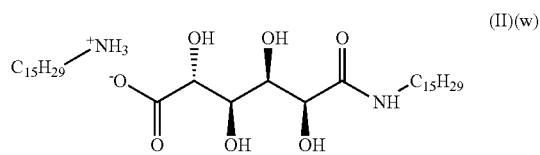
(II)(w)

In another embodiment, the compound of general formula (II) is hexadecenylammonium hexadecenylglucaramide (II)(x), also interchangeably referred as hexadecenylammonium (2R,3R,4R,5S)-6-(hexadecenylamino)-2,3,4,5-tetrahydroxy-6-oxohexanoate, and is represented as shown hereinbelow

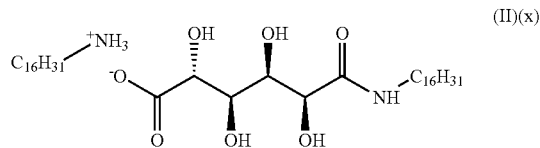
(II)(x)

In another embodiment, the compound of general formula (II) is heptadecenylammonium heptadecenylglucaramide (II)(y), also interchangeably referred as heptadecenylammonium (2R,3R,4R,5S)-6-(heptadecenylamino)-2,3,4,5-tetrahydroxy-6-oxohexanoate, and is represented as shown hereinbelow

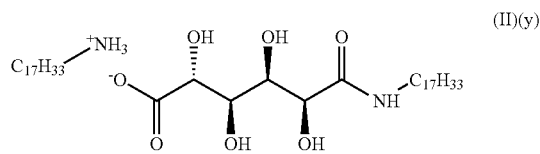
(II)(y)

In another embodiment, the compound of general formula (II) is octadecenylammonium octadecenylglucaramide (II)(z), also interchangeably referred as octadecenylammonium (2R,3R,4R,5S)-6-(octadecenylamino)-2,3,4,5-tetrahydroxy-6-oxohexanoate, and is represented as shown hereinbelow

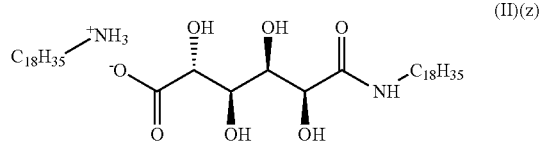
(II)(z)

Yet another aspect of the present invention describes the compounds of general formula (III)

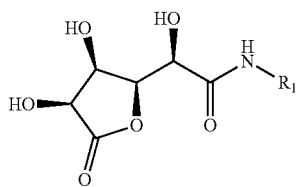

(III)

wherein, $R_1$ denotes unsubstituted, linear or branched, alkyl or alkenyl having 4 to ≤22 carbon atoms.

The compound of general formula (III), as described hereinabove, has an unsubstituted, linear or branched, alkyl or alkenyl having 4 to 22 carbon atoms, as denoted by $R_1$. For the purpose of the present invention, the compound of general formula (III) may also be interchangeably referred as alkylglucaramidolactone or alkenylglucaramidolactone.

Preferably, in the compound of general formula (III), as described hereinabove, $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (III) is hexylglucaramidolactone (III)(a), also interchangeably referred as (2R)-2-[(2S,3R,4S)-3,4-dihydroxy-5-oxo-tetrahydrofuran-2-yl]-N-hexyl-2-hydroxy-acetamide, and is represented as shown hereinbelow

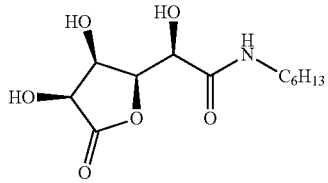

(III)(a)

In another embodiment, the compound of general formula (III) is heptylglucaramidolactone (III)(b), also interchangeably referred as (2R)-2-[(2S,3R,4S)-3,4-dihydroxy-5-oxo-tetrahydrofuran-2-yl]-N-heptyl-2-hydroxy-acetamide, and is represented as shown hereinbelow

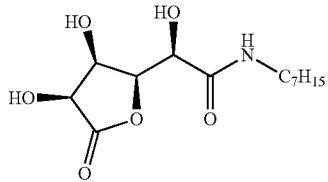

(III)(b)

In another embodiment, the compound of general formula (III) is octylglucaramidolactone (III)(c), also interchangeably referred as (2R)-2-[(2S,3R,4S)-3,4-dihydroxy-5-oxo-tetrahydrofuran-2-yl]-2-hydroxy-N-octyl-acetamide, and is represented as shown hereinbelow

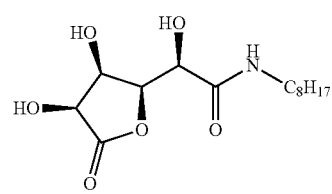

(III)(c)

In another embodiment, the compound of general formula (III) is nonylglucaramidolactone (III)(d), also interchangeably referred as (2R)-2-[(2S,3R,4S)-3,4-dihydroxy-5-oxo-tetrahydrofuran-2-yl]-2-hydroxy-N-nonyl-acetamide, and is represented as shown hereinbelow

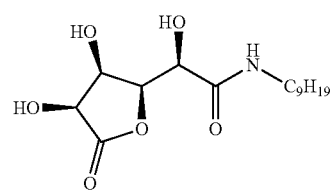

(III)(d)

In another embodiment, the compound of general formula (III) is decylglucaramidolactone (III)(e), also interchangeably referred as (2R)-2-[(2S,3R,4S)-3,4-dihydroxy-5-oxo-tetrahydrofuran-2-yl]-2-hydroxy-N-decyl-acetamide, and is represented as shown hereinbelow

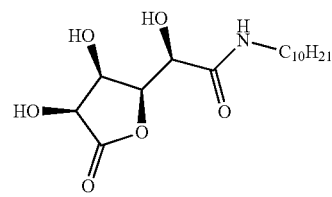

(III)(e)

In another embodiment, the compound of general formula (III) is undecylglucaramidolactone (III)(f), also interchangeably referred as (2R)-2-[(2S,3R,4S)-3,4-dihydroxy-5-oxo-tetrahydrofuran-2-yl]-2-hydroxy-N-undecyl-acetamide, and is represented as shown hereinbelow

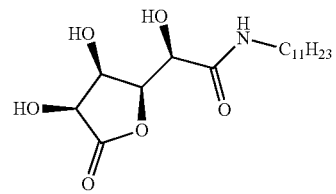

(III)(f)

In another embodiment, the compound of general formula (III) is dodecylglucaramidolactone (III)(g), also interchangeably referred as (2R)-2-[(2S,3R,4S)-3,4-dihydroxy-5-oxo-tetrahydrofuran-2-yl]-N-dodecyl-2-hydroxy-acetamide, and is represented as shown hereinbelow

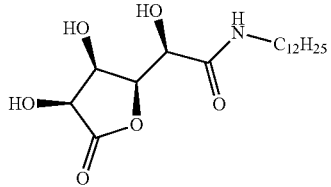
(III)(g)

In another embodiment, the compound of general formula (III) is tridecylglucaramidolactone (III)(h), also interchangeably referred as (2R)-2-[(2S,3R,4S)-3,4-dihydroxy-5-oxo-tetrahydrofuran-2-yl]-2-hydroxy-N-tridecyl-acetamide, and is represented as shown hereinbelow

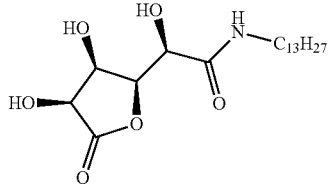
(III)(h)

In another embodiment, the compound of general formula (III) is tetradecylglucaramidolactone (III)(i), also interchangeably referred as (2R)-2-[(2S,3R,4S)-3,4-dihydroxy-5-oxo-tetrahydrofuran-2-yl]-2-hydroxy-N-tetradecyl-acetamide, and is represented as shown hereinbelow

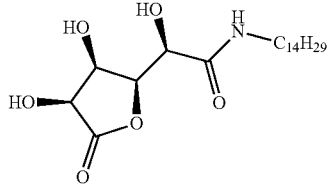
(III)(i)

In another embodiment, the compound of general formula (III) is pentadecylglucaramidolactone (III)(j), also interchangeably referred as (2R)-2-[(2S,3R,4S)-3,4-dihydroxy-5-oxo-tetrahydrofuran-2-yl]-2-hydroxy-N-pentadecyl-acetamide, and is represented as shown hereinbelow

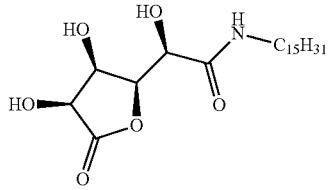
(III)(j)

In another embodiment, the compound of general formula (III) is hexadecylglucaramidolactone (III)(k), also interchangeably referred as (2R)-2-[(2S,3R,4S)-3,4-dihydroxy-5-oxo-tetrahydrofuran-2-yl]-N-hexadecyl-2-hydroxy-acetamide, and is represented as shown hereinbelow

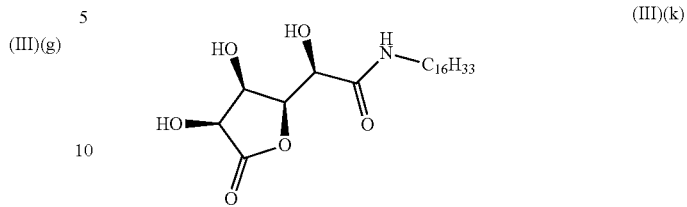
(III)(k)

In another embodiment, the compound of general formula (III) is heptadecylglucaramidolactone (III)(l), also interchangeably referred as (2R)-2-[(2S,3R,4S)-3,4-dihydroxy-5-oxo-tetrahydrofuran-2-yl]-N-heptadecyl-2-hydroxy-acetamide, and is represented as shown hereinbelow

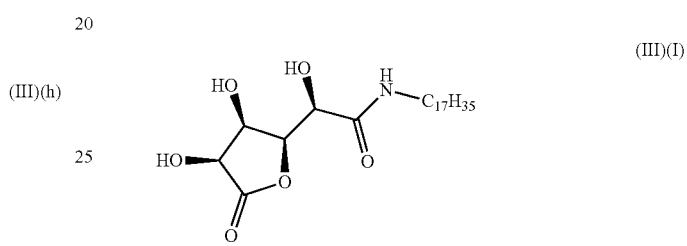
(III)(l)

In another embodiment, the compound of general formula (III) is octadecylglucaramidolactone (III)(m), also interchangeably referred as (2R)-2-[(2S,3R,4S)-3,4-dihydroxy-5-oxo-tetrahydrofuran-2-yl]-2-hydroxy-N-octadecyl-acetamide, and is represented as shown hereinbelow

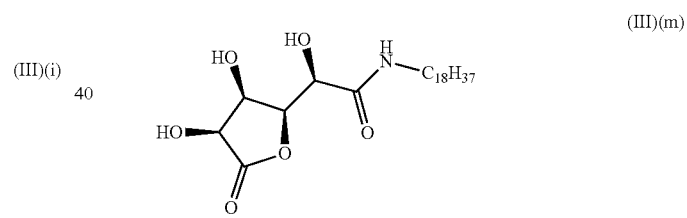
(III)(m)

In another embodiment, the compound of general formula (III) is hexenylglucaramidolactone (III)(n), also interchangeably referred as (2R)-2-[(2S,3R,4S)-3,4-dihydroxy-5-oxo-tetrahydrofuran-2-yl]-N-hexenyl-2-hydroxy-acetamide, and is represented as shown hereinbelow

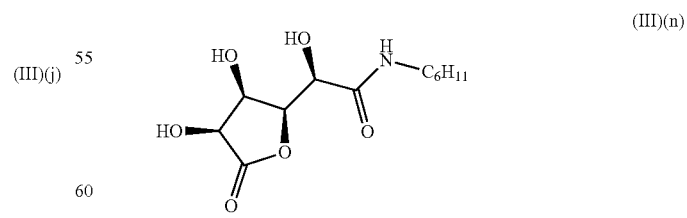
(III)(n)

In another embodiment, the compound of general formula (III) is heptenylglucaramidolactone (III)(o), also interchangeably referred as (2R)-2-[(2S,3R,4S)-3,4-dihydroxy-5-oxo-tetrahydrofuran-2-yl]-N-heptenyl-2-hydroxy-acetamide, and is represented as shown hereinbelow

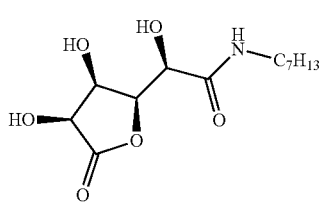
(III)(o)

In another embodiment, the compound of general formula (III) is octenylglucaramidolactone (III)(p), also interchangeably referred as (2R)-2-[(2S,3R,4S)-3,4-dihydroxy-5-oxo-tetrahydrofuran-2-yl]-2-hydroxy-N-octenyl-acetamide, and is represented as shown hereinbelow

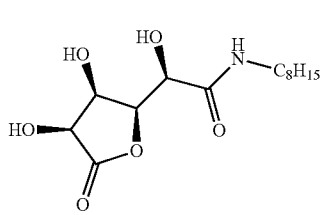
(III)(p)

In another embodiment, the compound of general formula (III) is nonenylglucaramidolactone (III)(q), also interchangeably referred as (2R)-2-[(2S,3R,4S)-3,4-dihydroxy-5-oxo-tetrahydrofuran-2-yl]-2-hydroxy-N-nonenyl-acetamide, and is represented as shown hereinbelow

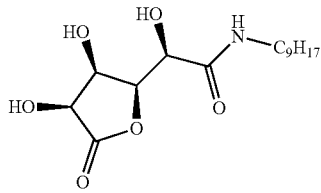
(III)(q)

In another embodiment, the compound of general formula (III) is decenylglucaramidolactone (III)(r), also interchangeably referred as (2R)-2-[(2S,3R,4S)-3,4-dihydroxy-5-oxo-tetrahydrofuran-2-yl]-2-hydroxy-N-decenyl-acetamide, and is represented as shown hereinbelow

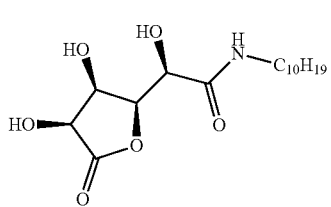
(III)(r)

In another embodiment, the compound of general formula (III) is undecenylglucaramidolactone (III)(s), also interchangeably referred as (2R)-2-[(2S,3R,4S)-3,4-dihydroxy-5-oxo-tetrahydrofuran-2-yl]-2-hydroxy-N-undecenyl-acetamide, and is represented as shown hereinbelow

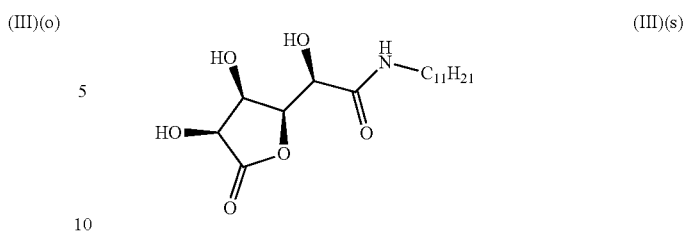
(III)(s)

In another embodiment, the compound of general formula (III) is dodecenylglucaramidolactone (III)(t), also interchangeably referred as (2R)-2-[(2S,3R,4S)-3,4-dihydroxy-5-oxo-tetrahydrofuran-2-yl]-N-dodecenyl-2-hydroxy-acetamide, and is represented as shown hereinbelow

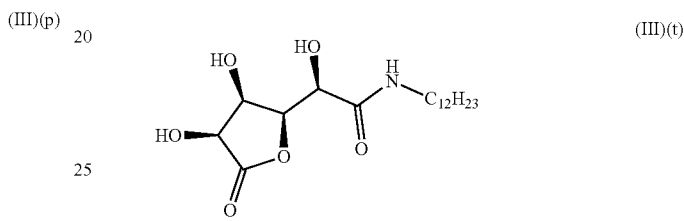
(III)(t)

In another embodiment, the compound of general formula (III) is tridecenylglucaramidolactone (III)(u), also interchangeably referred as (2R)-2-[(2S,3R,4S)-3,4-dihydroxy-5-oxo-tetrahydrofuran-2-yl]-2-hydroxy-N-tridecenyl-acetamide, and is represented as shown hereinbelow

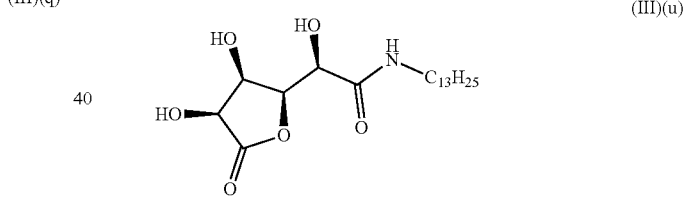
(III)(u)

In another embodiment, the compound of general formula (III) is tetradecenylglucaramidolactone (III)(v), also interchangeably referred as (2R)-2-[(2S,3R,4S)-3,4-dihydroxy-5-oxo-tetrahydrofuran-2-yl]-2-hydroxy-N-tetradecenyl-acetamide, and is represented as shown hereinbelow

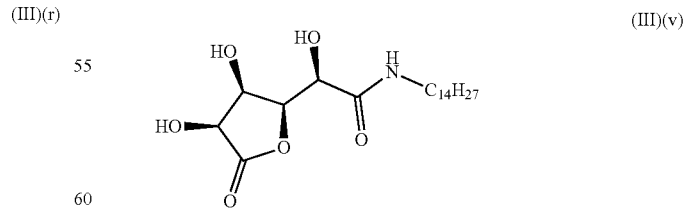
(III)(v)

In another embodiment, the compound of general formula (III) is pentadecenylglucaramidolactone (III)(w), also interchangeably referred as (2R)-2-[(2S,3R,4S)-3,4-dihydroxy-5-oxo-tetrahydrofuran-2-yl]-2-hydroxy-N-pentadecenyl-acetamide, and is represented as shown hereinbelow

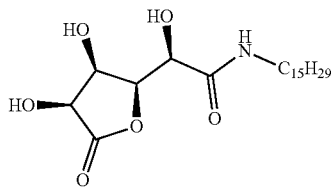

(III)(w)

In another embodiment, the compound of general formula (III) is hexadecenylglucaramidolactone (III)(x), also interchangeably referred as (2R)-2-[(2S,3R,4S)-3,4-dihydroxy-5-oxo-tetrahydrofuran-2-yl]-N-hexadecenyl-2-hydroxy-acetamide, and is represented as shown hereinbelow

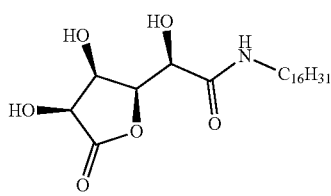

(III)(x)

In another embodiment, the compound of general formula (III) is heptadecenylglucaramidolactone (III)(y), also interchangeably referred as (2R)-2-[(2S,3R,4S)-3,4-dihydroxy-5-oxo-tetrahydrofuran-2-yl]-N-heptadecenyl-2-hydroxy-acetamide, and is represented as shown hereinbelow

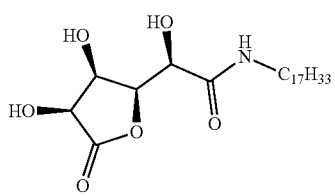

(III)(y)

In another embodiment, the compound of general formula (III) is octadecenylglucaramidolactone (III)(z), also interchangeably referred as (2R)-2-[(2S,3R,4S)-3,4-dihydroxy-5-oxo-tetrahydrofuran-2-yl]-2-hydroxy-N-octadecenyl-acetamide, and is represented as shown hereinbelow

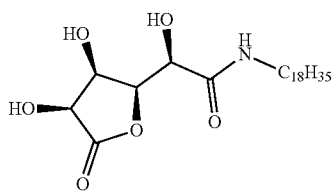

(III)(z)

Still another aspect of the present invention describes the compounds of general formula (IV)

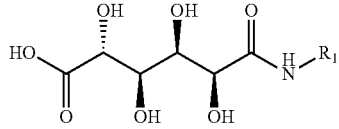

(IV)

wherein, $R_1$ denotes unsubstituted, linear or branched, alkyl or alkenyl having 4 to 22 carbon atoms.

The compounds of general formula (IV), as described hereinabove, may be interchangeably also referred as alkylamidoglucaric acid. Preferably, in the compound of general formula (IV), $R_1$ denotes unsubstituted, linear or branched, alkyl or alkenyl having 5 to 22 carbon atoms. More preferably, $R_1$ denotes unsubstituted, linear or branched, alkyl or alkenyl having 5 to 20 carbon atoms. Most preferably, $R_1$ denotes unsubstituted, linear or branched, alkyl or alkenyl having 6 to 20 carbon atoms. In a particularly preferable embodiment, $R_1$ denotes unsubstituted, linear, alkyl or alkenyl having 6 to 18 carbon atoms. The $R_1$ denoting the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, octadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

Accordingly, in an embodiment the compound of general formula (IV) is hexylamidoglucaric acid (IV)(a), also interchangeably referred as (2R,3R,4R,5S)-6-(hexylamino)-2,3,4,5-tetrahydroxy-6-oxo-hexanoic acid, and is represented as shown hereinbelow

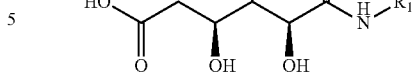

(IV)(a)

In another embodiment, the compound of general formula (IV) is heptylamidoglucaric acid (IV)(b), also interchangeably referred as (2R,3R,4R,5S)-6-(heptylamino)-2,3,4,5-tetrahydroxy-6-oxo-hexanoic acid, and is represented as shown hereinbelow

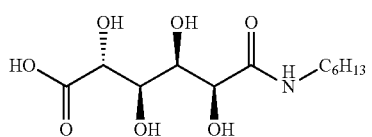

(IV)(b)

In another embodiment, the compound of general formula (IV) is octylamidoglucaric acid (IV)(c), also interchangeably referred as (2R,3R,4R,5S)-6-(octylamino)-2,3,4,5-tetrahydroxy-6-oxo-hexanoic acid, and is represented as shown hereinbelow

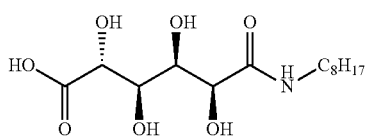
(IV)(c)

In another embodiment, the compound of general formula (IV) is nonylamidoglucaric acid (IV)(d), also interchangeably referred as (2R,3R,4R,5S)-6-(nonylamino)-2,3,4,5-tetrahydroxy-6-oxo-hexanoic acid, and is represented as shown hereinbelow

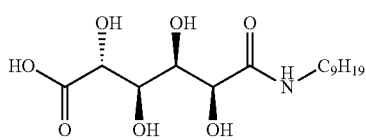
(IV)(d)

In another embodiment, the compound of general formula (IV) is decylamidoglucaric acid (III)(e), also interchangeably referred as (2R,3R,4R,5S)-6-(decylamino)-2,3,4,5-tetrahydroxy-6-oxo-hexanoic acid, and is represented as shown hereinbelow

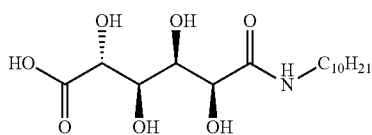
(IV)(e)

In another embodiment, the compound of general formula (IV) is undecylamidoglucaric acid (IV)(f), also interchangeably referred as (2R,3R,4R,5S)-6-(undecylamino)-2,3,4,5-tetrahydroxy-6-oxo-hexanoic acid, and is represented as shown hereinbelow

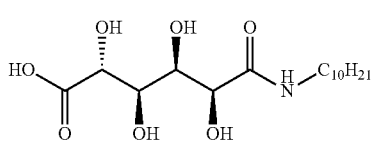
(IV)(f)

In another embodiment, the compound of general formula (IV) is dodecylamidoglucaric acid (IV)(g), also interchangeably referred as (2R,3R,4R,5S)-6-(dodecylamino)-2,3,4,5-tetrahydroxy-6-oxo-hexanoic acid, and is represented as shown hereinbelow

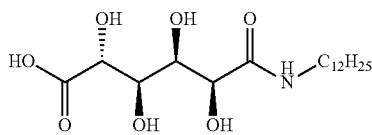
(IV)(g)

In another embodiment, the compound of general formula (IV) is tridecylamidoglucaric acid (IV)(h), also interchangeably referred as (2R,3R,4R,5S)-6-(tridecylamino)2,3,4,5-tetrahydroxy-6-oxo--hexanoic acid, and is represented as shown hereinbelow

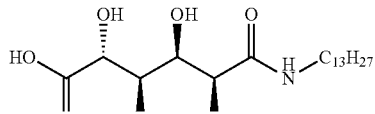
(IV)(h)

In another embodiment, the compound of general formula (IV) is tetradecylamidoglucaric acid (IV)(i), also interchangeably referred as (2R,3R,4R,5S)-6-(tetradecylamino)-2,3,4,5-tetrahydroxy-6-oxo-hexanoic acid, and is represented as shown hereinbelow

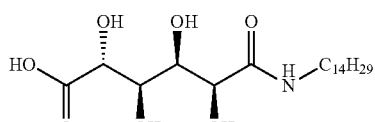
(IV)(i)

In another embodiment, the compound of general formula (IV) is pentadecylamidoglucaric acid (IV)(j), also interchangeably referred as (2R,3R,4R,5S)-6-(pentadecylamino) 2,3,4,5-tetrahydroxy-6-oxo--hexanoic acid, and is represented as shown hereinbelow

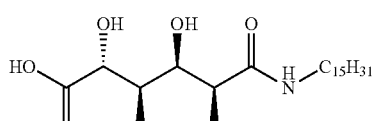
(IV)(j)

In another embodiment, the compound of general formula (IV) is hexadecylamidoglucaric acid (IV)(k), also interchangeably referred as (2R,3R,4R,5S)-6-(hexadecylamino)-2,3,4,5-tetrahydroxy-6-oxo-hexanoic acid, and is represented as shown hereinbelow

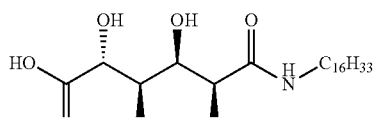
(IV)(k)

In another embodiment, the compound of general formula (IV) is heptadecylamidoglucaric acid (IV)(l), also interchangeably referred as (2R,3R,4R,5S)-6-(heptadecylamino)-2,3,4,5-tetrahydroxy-6-oxo-hexanoic acid, and is represented as shown hereinbelow

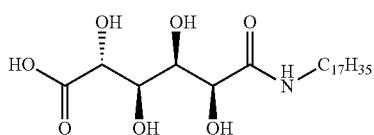

In another embodiment, the compound of general formula (IV) is octadecylamidoglucaric acid (IV)(m), also interchangeably referred as (2R,3R,4R,5S)-6-(octadecylamino)-2,3,4,5-tetrahydroxy-6-oxo-hexanoic acid, and is represented as shown hereinbelow

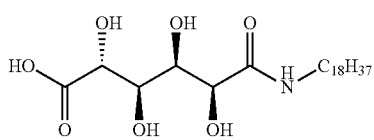

In another embodiment, the compound of general formula (IV) is hexenylamidoglucaric acid (IV)(n), also interchangeably referred as (2R,3R,4R,5S)-6-(hexenylamino)-2,3,4,5-tetrahydroxy-6-oxo-hexanoic acid, and is represented as shown hereinbelow

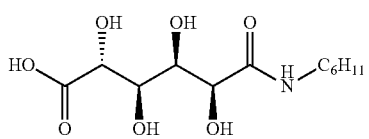

In another embodiment, the compound of general formula (IV) is heptenylamidoglucaric acid (IV)(o), also interchangeably referred as (2R,3R,4R,5S)-6-(heptenylamino)-2,3,4,5-tetrahydroxy-6-oxo-hexanoic acid, and is represented as shown hereinbelow

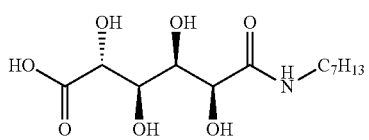

In another embodiment, the compound of general formula (IV) is octenylamidoglucaric acid (IV)(p), also interchangeably referred as (2R,3R,4R,5S)-6-(octenylamino)-2,3,4,5-tetrahydroxy-6-oxo-hexanoic acid, and is represented as shown hereinbelow

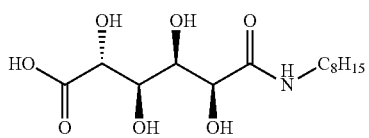

In another embodiment, the compound of general formula (IV) is nonenylamidoglucaric acid (IV)(q), also interchangeably referred as (2R,3R,4R,5S)-6-(nonenylamino)-2,3,4,5-tetrahydroxy-6-oxo-hexanoic acid, and is represented as shown hereinbelow

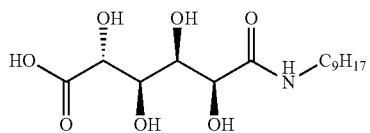

In another embodiment, the compound of general formula (IV) is decenylamidoglucaric acid (III)(r), also interchangeably referred as (2R,3R,4R,5S)-6-(decenylamino)-2,3,4,5-tetrahydroxy-6-oxo-hexanoic acid, and is represented as shown hereinbelow

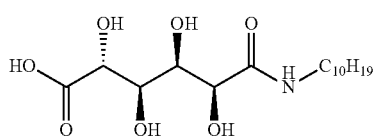

In another embodiment, the compound of general formula (IV) is undecenylamidoglucaric acid (IV)(s), also interchangeably referred as (2R,3R,4R,5S)-6-(undecenylamino)-2,3,4,5-tetrahydroxy-6-oxo-hexanoic acid, and is represented as shown hereinbelow

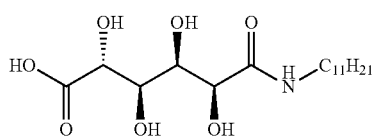

In another embodiment, the compound of general formula (IV) is dodecenylamidoglucaric acid (IV)(t), also interchangeably referred as (2R,3R,4R,5S)-6-(dodecenylamino)-2,3,4,5-tetrahydroxy-6-oxo-hexanoic acid, and is represented as shown hereinbelow

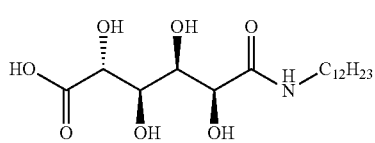

In another embodiment, the compound of general formula (IV) is tridecenylamidoglucaric acid (IV)(u), also interchangeably referred as (2R,3R,4R,5S)-6-(tridecenylamino)-2,3,4,5-tetrahydroxy-6-oxo-hexanoic acid, and is represented as shown hereinbelow

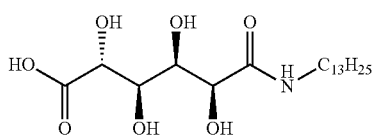

(IV)(u)

In another embodiment, the compound of general formula (IV) is tetradecenylamidoglucaric acid (IV)(v), also interchangeably referred as (2R,3R,4R,5S)-6-(tetradecenylamino)-2,3,4,5-tetrahydroxy-6-oxo-hexanoic acid, and is represented as shown hereinbelow

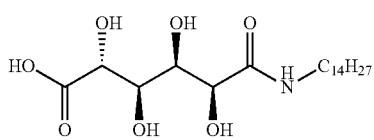

(IV)(v)

In another embodiment, the compound of general formula (IV) is pentadecenylamidoglucaric acid (IV)(w), also interchangeably referred as (2R,3R,4R,5S)-6-(pentadecenylamino)-2,3,4,5-tetrahydroxy-6-oxo-hexanoic acid, and is represented as shown hereinbelow

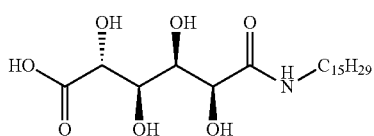

(IV)(w)

In another embodiment, the compound of general formula (IV) is hexadecenylamidoglucaric acid (IV)(x), also interchangeably referred as (2R,3R,4R,5S)-6-(hexadecenylamino)-2,3,4,5-tetrahydroxy-6-oxo-hexanoic acid, and is represented as shown hereinbelow

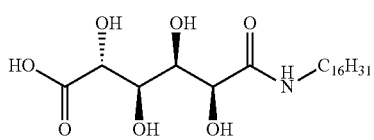

(IV)(x)

In another embodiment, the compound of general formula (IV) is heptadecenylamidoglucaric acid (IV)(y), also interchangeably referred as (2R,3R,4R,5S)-6-(heptadecenylamino)-2,3,4,5-tetrahydroxy-6-oxo-hexanoic acid, and is represented as shown hereinbelow

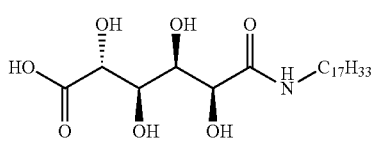

(IV)(y)

In another embodiment, the compound of general formula (IV) is octadecenylamidoglucaric acid (IV)(z), also interchangeably referred as (2R,3R,4R,5S)-6-(octadecenylamino)-2,3,4,5-tetrahydroxy-6-oxo-hexanoic acid, and is represented as shown hereinbelow

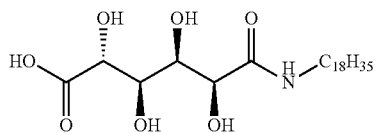

(IV)(z)

The compounds of the present invention, such as but not limited to the compound of general formula (III) and the compound of general formula (IV), as described hereinabove find wide application, such as but not limited to, as a surfactant, emulsifier, solubilizer, rheology modifier and gelator. This may be attributed to the fact that the long carbon chain represented by $R_1$ in the compounds as described hereinabove imparts hydrophobicity to the compounds, while the remaining moiety imparts water-solubility and hydrophilic nature to the compounds. This amphiphilic nature in the compounds enables them for application particularly as surfactants and/or emulsifiers. Accordingly, the present invention provides easy tunability in terms of the required hydrophobic property in the final compound which can be adjusted as per the desired application by controlling the chain length of the amine of general formula (I) i.e. by controlling $R_1$.

The present invention is illustrated in more detail by the following embodiments and combinations of embodiments which result from the corresponding dependency references and links:

1. A process for preparing D-glucaro-6,3-lactone monoamide, comprising the steps of:

A) adding an amine of general formula (I)

$R_1$—$NH_2$ (I), wherein $R_1$ denotes unsubstituted, linear or branched, alkyl or alkenyl having 4 to 22 carbon atoms, to an aqueous solution of a salt of D-glucaro-6,3-lactone and heating at a temperature in the range of ≥40° C. to ≤90° C., to obtain a compound of general formula (II)

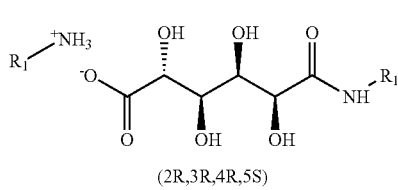

(II)

(2R,3R,4R,5S)

wherein, $R_1$ denotes unsubstituted, linear or branched, alkyl or alkenyl having 4 to 22 carbon atoms, and B) treating the compound of general formula (II) with an acid to obtain a compound of general formula (III)

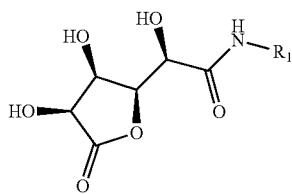

(III)

wherein,
R₁ denotes unsubstituted, linear or branched, alkyl or alkenyl having 4 to 22 carbon atoms.

2. The process according to embodiment 1, characterized in that in step (A) the amine of general formula (I) is present as a mixture with at least one polar solvent.

3. The process according to embodiment 1 or 2, characterized in that in step (A) the at least one polar solvent is selected from the group consisting of ethers and alcohols.

4. The process according to one or more of embodiments 1 to 3, characterized in that in step (A) the at least one polar solvent is at least one alcohol solvent.

5. The process according to embodiment 3, characterized in that in step (A) the ethers are selected from the group consisting of methyl tert-butyl ether, dioxane, tetrahydrofuran and tetrahydropyran.

6. The process according to embodiment 4, characterized in that in step (A) the at least one alcohol solvent is selected from the group consisting of ethanol, methanol, n-butanol, isobutanol, sec-butanol, n-propanol, iso-propanol, pentanol and hexanol.

7. The process according to one or more of embodiments 1 to 6, characterized in that R₁ denotes unsubstituted, linear or branched, alkyl or alkenyl having 6 to 18 carbon atoms.

8. The process according to embodiment 7, characterized in that R₁ denotes unsubstituted, linear, alkyl or alkenyl having 6 to 18 carbon atoms.

9. The process according to embodiment 8, characterized in that the unsubstituted, linear, alkyl or alkenyl having 6 to 18 carbon atoms is selected from the group consisting of hexyl, heptyl, octyl, nonyl, decyl, undecyl, dodecyl, tridecyl, tetradecyl, pentadecyl, hexadecyl, heptadecyl, octadecyl, hexenyl, heptenyl, octenyl, nonenyl, decenyl, undecenyl, dodecenyl, tridecenyl, tetradecenyl, pentadecenyl, hexadecenyl, heptadecenyl and octadecenyl.

10. The process according to one or more of embodiments 1 to 9, characterized in that in step (A) the weight ratio between the at least one polar solvent and the amine of general formula (I) is in the range of ≥1:5 to ≤5:1.

11. The process according to one or more of embodiments 1 to 10, characterized in that in step (A) the salt of D-glucaro-6,3-lactone is selected from the group consisting of calcium glucaro-6,3-lactone, potassium glucaro-6,3-lactone, sodium glucaro-6,3-lactone, lithium glucaro-6,3-lactone and magnesium glucaro-6,3-lactone.

12. The process according to one or more of embodiments 1 to 11, characterized in that in step (A) the salt of D-glucaro-6,3-lactone is sodium glucaro-6,3-lactone.

13. The process according to one or more of embodiments 1 to 12, characterized in that in step (A) the molar ratio between the amine of general formula (I) and the aqueous solution of the salt of D-glucaro-6,3-lactone is in the range of ≥1:1 to ≤10:1.

14. The process according to one or more of embodiments 1 to 13, characterized in that in step (A) the aqueous solution of the salt of D-glucaro-6,3-lactone has a weight ratio between water and the salt of D-glucaro-6,3-lactone in the range of ≥1:1 to ≤15:1.

15. The process according to one or more of embodiments 1 to 14, characterized in that a temperature in the range of ≥5° C. to ≤30° C. for a duration in the range of ≥0.1 h to ≤5 h is provided while adding the amine of general formula (I) to the aqueous solution of the salt of D-glucaro-6,3-lactone in step (A).

16. The process according to one or more of embodiments 1 to 15, characterized in that in step (A) the compound of general formula (II) is obtained by:
    (A1) heating a mixture comprising the amine of general formula (I) and the aqueous solution of the salt of D-glucaro-6,3-lactone at a temperature in the range of ≥40° C. to ≤90° C. to obtain a precipitate,
    (A2) filtrating the precipitate of step (A1) and washing with the at least one polar solvent to obtain a crude mixture and a mother liquor,
    (A3) optionally storing the mother liquor of step (A2) at a temperature in the range of ≥0° C. to ≤30° C. for a period in the range of ≥8 h to ≤15 h to obtain a crude mixture, and
    (A4) drying the crude mixture of step (A2) or optionally step (A3) to obtain the compound of general formula (II).

17. The process according to embodiment 16, characterized in that in step (A2) the washing with the at least one polar solvent is carried out at a temperature in the range of ≥5° C. to ≤30° C.

18. The process according to embodiment 17, characterized in that in step (A2) the weight ratio between the at least one polar solvent and the precipitate is in the range of ≥1:15 to ≤15:1.

19. The process according to one or more of embodiments 1 to 18, characterized in that in step (B) the acid is selected from the group consisting of organic acid and inorganic acid.

20. The process according to embodiment 19, characterized in that in step (B) the acid is an organic acid.

21. The process according to embodiment 20, characterized in that the organic acid is an acidic ion exchange resin.

22. The process according to embodiment 21, characterized in that the acidic ion exchange resin comprises a crosslinked copolymer matrix functionalized with an organic acid selected from the group consisting of carboxylic acid and sulfonic acid.

23. The process according to embodiment 22, characterized in that the acidic ion-exchange resin has a concentration of active sites in the range of ≥1 eq/kg to ≤10 eq/kg.

24. The process according to one or more of embodiments 1 to 23, characterized in that in step (B) the weight ratio between the acid and the compound of general formula (II) is in the range of ≥1:10 to ≤10:1.

25. The process according to one or more of embodiments 1 to 24, characterized in that in step (B) the compound of general formula (II) is dissolved in the at least one polar solvent.

26. The process according to embodiment 25, characterized in that in step (B) the at least one polar solvent is at least one ether solvent.

27. The process according to embodiment 26, characterized in that in step (B) the at least one ether solvent is selected from the group consisting of methyl tert-butyl ether, dioxane, tetrahydrofuran and tetrahydropyran.

28. The process according to one or more of embodiments 25 to 27, characterized in that in step (B) the weight ratio between the at least one polar solvent and the compound of general formula (II) is in the range of ≥5:1 to ≤100:1.

29. The process according to one or more of embodiments 1 to 28, characterized in that in step (B) a temperature in the range of ≥10° C. to ≤60° C. is provided.

30. The process according to one or more of embodiments 1 to 29, characterized in that in step (A), step (A1) and step (B), independently of one another, stirring is carried out at a rotational speed in the range of ≥100 rpm to ≤1000 rpm for a period in the range of ≥0.1 h to ≤24 h.

31. The process according to one or more of embodiments 1 to 30 further comprising the step of:
   C) drying the compound of general formula (III) obtained in step (B).

32. The process according to one or more of embodiments 1 to 31, characterized in that the step (B) further comprises a compound of general formula (IV)

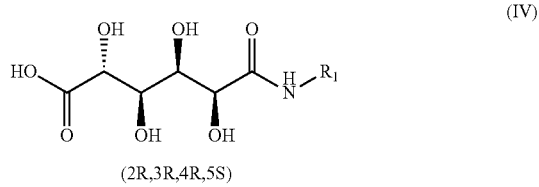

(2R,3R,4R,5S)

wherein,
   $R_1$ denotes unsubstituted, linear or branched, alkyl or alkenyl having 4 to 22 carbon atoms.

33. The process according to one or more of embodiments 1 to 32, characterized in that in step (A4) and step (C) the drying is carried out, independently of one another, under vacuum pressure in the range of ≥0.1 mbar to ≤500 mbar and at a temperature in the range of ≥20° C. to ≤80° C.

34. A compound of general formula (II)

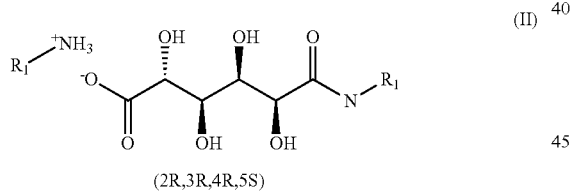

(2R,3R,4R,5S)

wherein,
   $R_1$ denotes unsubstituted, linear or branched, alkyl or alkenyl having 4 to 22 carbon atoms.

35. The compound according to embodiment 34, characterized in that $R_1$ denotes unsubstituted, linear, alkyl or alkenyl having 6 to 18 carbon atoms.

36. The compound according to embodiment 34 selected from the group consisting of hexylammonium (2R,3R,4R,5S)-6-(hexylamino)-2,3,4,5-tetrahydroxy-6-oxohexanoate, heptylammonium (2R,3R,4R,5S)-6-(heptylamino)-2,3,4,5-tetrahydroxy-6-oxohexanoate, octylammonium (2R,3R,4R,5S)-6-(octylamino)-2,3,4,5-tetrahydroxy-6-oxohexanoate, nonylammonium (2 R,3R,4 R,5S)-6-(nonylamino)-2,3,4,5-tetrahydroxy-6-oxohexanoate, decylammonium (2R,3R,4R,5S)-6-(decylamino)-2,3,4,5-tetrahydroxy-6-oxohexanoate, undecylammonium (2R,3R,4R,5S)-6-(undecylamino)-2,3,4,5-tetrahydroxy-6-oxohexanoate, dodecylammonium (2R,3R,4R,5S)-6-(dodecylamino)-2,3,4,5-tetrahydroxy-6-oxohexanoate, tridecylammonium (2R,3R,4R,5S)-6-(tridecylamino)-2,3,4,5-tetrahydroxy-6-oxohexanoate, tetradecylammonium (2R,3R,4R,5S)-6-(tetradecylamino)-2,3,4,5-tetrahydroxy-6-oxohexanoate, pentadecylammonium (2R,3R,4R,5S)-6-(pentadecylamino)-2,3,4,5-tetrahydroxy-6-oxohexanoate, hexadecylammonium (2R,3R,4R,5S)- 6-(hexadecylamino)-2,3,4,5-tetrahydroxy-6-oxohexanoate, heptadecylammonium (2R,3R,4R,5S)-6-(heptadecylamino)-2,3,4,5-tetrahydroxy-6-oxohexanoate, octadecylammonium (2R,3R,4R,5S)-6-(octadecylamino)-2,3,4,5-tetrahydroxy-6-oxohexanoate, hexenylammonium (2R,3R,4R,5S)-6-(hexenylamino)-2,3,4,5-tetrahydroxy-6-oxohexanoate, heptenylammonium (2R,3R,4R,5S)-6-(heptenylamino)-2,3,4,5-tetrahydroxy-6-oxohexanoate, octenylammonium (2R,3R,4R,5S)-6-(octenylamino)-2,3,4,5-tetrahydroxy-6-oxohexanoate, nonenylammonium (2R,3R,4R,5S)-6-(nonenylamino)-2,3,4,5-tetrahydroxy-6-oxohexanoate, decenylammonium (2R,3R,4R,5S)-6-(decenylamino)-2,3,4,5-tetrahydroxy-6-oxohexanoate, undecenylammonium (2R,3R,4R,5S)-6-(undecenylamino)-2,3,4,5-tetrahydroxy-6-oxohexanoate, dodecenylammonium (2R,3R,4R,5S)-6-(dodecenylamino)-2,3,4,5-tetrahydroxy-6-oxohexanoate, tridecenylammonium (2R,3R,4R,5S)-6-(tridecenylamino)-2,3,4,5-tetrahydroxy-6-oxohexanoate, tetradecenylammonium (2R,3R,4R,5S)-6-(tetradecenylamino)-2,3,4,5-tetrahydroxy-6-oxohexanoate, pentadecenylammonium (2R,3R,4R,5S)-6-(pentadecenylamino)-2,3,4,5-tetra hydroxy-6-oxohexanoate, hexadecenylammonium (2R,3R,4R,5S)-6-(hexadecenylamino)-2,3,4,5-tetrahydroxy-6-oxohexanoate, heptadecenylammonium (2R,3R,4R,5S)-6-(heptadecenylamino)-2,3,4,5-tetrahydroxy-6-oxohexanoate and octadecenylammonium (2R,3R,4R,5S)-6-(octadecenylamino)-2,3,4,5-tetrahydroxy-6-oxohexanoate.

37. A compound of general formula (III)

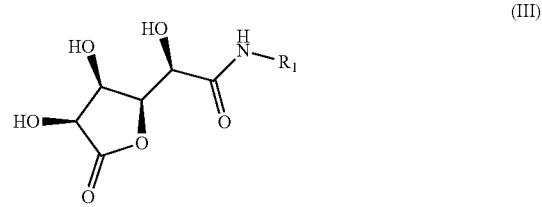

wherein,
   $R_1$ denotes unsubstituted, linear or branched, alkyl or alkenyl having 4 to 22 carbon atoms.

38. The compound according to embodiment 37, characterized in that $R_1$ denotes unsubstituted, linear, alkyl or alkenyl having 6 to 18 carbon atoms.

39. The compound according to embodiment 37 selected from the group consisting of (2R)-2-[(2S,3R,4S)-3,4-dihydroxy-5-oxo-tetrahydrofuran-2-yl]-N-hexyl-2-hydroxy-acetamide, (2R)-2-[(2S,3R,4S)-3,4-dihydroxy-5-oxo-tetrahydrofuran-2-yl]-N-heptyl-2-hydroxy-acetamide, (2R)-2-[(2S,3R,4S)-3,4-dihydroxy-5-oxo-tetrahydrofuran-2-yl]-2-hydroxy-N-octyl-acetamide, (2R)-2-[(2S,3R,4S)-3,4-dihydroxy-5-oxo-tetrahydrofuran-2-yl]-2-hydroxy-N-nonyl-acetamide, (2R)-2-[(2S,3R,4S)-3,4-dihydroxy-5-oxo-tetrahydrofuran-2-yl]-2-hydroxy-N-decyl-acetamide, (2R)-2-[(2S,3R,4S)-3,4-dihydroxy-5-oxo-tetrahydrofuran-2-yl]-2-hydroxy-N-un-decyl-acetamide, (2R)-2-[(2S,3R,4S)-3,4-dihydroxy-5-oxo-tetrahydrofuran-2-yl]-N-dodecyl-2-hydroxy-acetamide, (2R)-2-[(2S,3R,4S)-3,4-dihydroxy-5-oxo-tetrahydrofuran-2-yl]-2-hydroxy-N-tridecyl-acetamide, (2R)-2-[(2S,3R,4S)-3,4-dihydroxy-5-oxo-tetrahydrofuran-2-yl]-2-hydroxy-N-tetradecyl-acetamide, (2R)-2-[(2S,3R,4S)-3,4-dihydroxy-5-oxo-tetrahydrofuran-2-yl]-2-hydroxy-N-pentadecyl-acetamide, (2R)-2-[(2S,3R,4S)-3,4-dihydroxy-5-oxo-tetrahydrofuran-2-yl]-N-hexadecyl-2-hydroxy-acetamide, (2R)-2-[(2S,3R,4S)-3,4-dihydroxy-5-oxo-tetrahydrofuran-2-yl]-N-heptadecyl-2-hydroxy-acetamide, (2R)-2-[(2S,3R,4S)-3,4-dihydroxy-5-oxo-tetrahydrofuran-2-yl]-2-hydroxy-N-octadecyl-acetamide, (2R)-2-[(2S,3R,4S)-3,4-dihydroxy-5-oxo-tetrahydrofuran-2-yl]-N-hexenyl-2-hydroxy-acetamide, (2R)-2-[(2S,3R,4S)-3,4-dihydroxy-5-oxo-tetrahydrofuran-2-yl]-N-heptenyl-2-hydroxy-acetamide, (2R)-2-[(2S,3R,4S)-3,4-dihydroxy-5-oxo-tetrahydrofuran-2-yl]-2-hydroxy-N-octenyl-acetamide, (2R)-2-[(2S,3R,4S)-3,4-dihydroxy-5-oxo-tetrahydrofuran-2-yl]-2-hydroxy-N-nonenyl-acetamide, (2R)-2-[(2S,3R,4S)-3,4-dihydroxy-5-oxo-tetrahydrofuran-2-yl]-2-hydroxy-N-decenyl-acetamide, (2R)-2-[(2S,3R,4S)-3,4-dihydroxy-5-oxo-tetrahydrofuran-2-yl]-2-hydroxy-N-undecenyl-acetamide, (2R)-2-[(2S,3R,4S)-3,4-dihydroxy-5-oxo-tetrahydrofuran-2-yl]-N-dodecenyl-2-hydroxy-acetamide, (2R)-2-[(2S,3R,4S)-3,4-dihydroxy-5-oxo-tetrahydrofuran-2-yl]-2-hydroxy-N-trid ecenyl-acetamide, (2R)-2-[(2S,3R,4S)-3,4-dihydroxy-5-oxo-tetrahydrofuran-2-yl]-2-hydroxy-N-tetradecenyl-acetamide, (2R)-2-[(2S,3R,4S)-3,4-dihydroxy-5-oxo-tetrahydrofuran-2-yl]-2-hydroxy-N-pentadecenyl-acetamide, (2R)-2-[(2S,3R,4S)-3,4-dihydroxy-5-oxo-tetrahydrofuran-2-yl]-N-hexadecenyl-2-hydroxy-acetamide, (2R)-2-[(2S,3R,4S)-3,4-dihydroxy-5-oxo-tetrahydrofuran-2-yl]-N-heptadecenyl-2-hydroxy-acetamide and (2R)-2-[(2S,3R,4S)-3 ,4-dihydroxy-5-oxo-tetrahydrofuran-2-yl]-2-hydroxy-N-octadecenyl-acetamide.

40. Use of the compound of general formula (III) according to one or more of embodiments 37 to 39 or as obtained by the process according to one or more of embodiments 1 to 33 as surfactant, emulsifier, solubilizer, rheology modifier and gelator.

EXAMPLES

Compounds

| | |
|---|---|
| Amine of general formula (I) | Octylamine |
| | Dodecylamine |
| | (Z)-Octadec-9-enylamine |
| Alcohol solvent | Methanol |
| Ether solvent | Tetrahydropyran |
| | Tetrahydrofuran |
| Acidic cation exchanger | Amberlyst ® 15 (sulfonic acid polymeric resin based on cross-linked styrene divinylbenzene copolymer) |
| are available from Sigma Aldrich. | |

D-glucaro-6,3-lactone was synthesized according to the procedure described in Chen and Kiely, J. Org. Chem. 1996, 61, 5847-5851.

Synthesis of Sodium Glucaro-6,3-Lactone 180 g of D-glucaro-6,3-lactone was dissolved in 408 g of deionized water with stirring at 20° C. for 1 h. 74.6 g of sodium acetate was added to this solution, which readily dissolved. The solution was set aside without stirring at room temperature with colourless crystals beginning to form within 20 min. The crystalline product was removed by filtration, washed with acetone and dried in vacuum. 172 g of sodium glucaro-6,3-lactone was obtained as colourless crystals with a yield of 88%. The NMR data corresponds well to that reported by Chen and Kiely, J. Org. Chem. 1996, 61, 5847-5851.

Synthesis of D-Glucaro-6,3-Lactone Monoamide from Sodium Glucaro-6,3-Lactone

Example 1

66.0 g of sodium glucaro-6,3-lactone was dissolved in 460 g water. 41.6 g of octylamine was added dropwise into 40.1 g of methanol over a duration of 30 min with stirring at 400 rpm. The dropping funnel was rinsed with additional 4.8 g of methanol. During the addition, the mixture was heated up by 11° C. and a colourless precipitate was formed. After complete addition, the reaction mixture was heated to 75° C. and stirred for 5 h. A colourless to off-white foam formed during heating up above 60° C., which dissolved again during the reaction time. The precipitate was collected by filtration over a glass filter P3 and washed with cold methanol (2×50 mL), resulting in 79.7 g of the crude mixture, still moist product. The mother liquor was stored overnight at 2° C., thereby resulting in another 9.2 g of the crude mixture. The crude mixtures were combined and dried in vacuum to obtain 49.2 g of octylammonium octylglucaramide (octylammonium (2R,3R,4R,5S)-6-(octylamino)-2,3,4,5-tetrahydroxy-6-oxohexanoate) as a colourless solid with a yield of 36%.

25.3 g of the octylammonium octylglucaramide was dissolved in 800 g of tetrahydropyran (THP). 27.5 g of Amberlyst® 15 in hydrogen form was added and the mixture was stirred at 40° C. for 8.5 h. After cooling to 20° C., the ion exchanger was filtered off and washed with THP (2×50 mL). The filtrate was dried in vacuum at 200 mbar and 60° C. Thereafter, the filtrate was kept overnight at 0.5 mbar, thereby giving 36.5 g of octylglucaramidolactone ((2R)-2-[(2S,3R,4S)-3,4-dihydroxy-5-oxo-tetrahydrofuran-2-yl]-2-hydroxy-N-octyl-acetamide) as a light yellow solid with a yield of 92% alongwith traces of octylamidoglucaric acid ((2R,3R,4R,5S)-6-(octylamino)-2,3,4,5-tetrahydroxy-6-oxo-hexanoic acid).

Example 2

66.0 g of sodium glucaro-6,3-lactone was dissolved in 416 g of water. 57.4 g of dodecylamine was added dropwise into 57.6 g of methanol over a duration of 20 min with stirring at 400 rpm. The dropping funnel was rinsed with additional 20 g of methanol. During the addition, the mixture was heated up by 15° C. and a colorless precipitate was formed. After complete addition, the reaction mixture was heated to 75° C. and stirred for 5 h. A colorless foam formed during heating above 60° C. This precipitate was collected by filtration over a glass filter P3 and washed with cold methanol (2×50mL) and dried in vacuum to obtain 108 g of dodecylammonium dodecylglucaramide (dodecylammonium (2R,3R,4R,5S)-6-(dodecylamino)-2,3,4,5-tetrahydroxy-6-oxohexanoate) as a colorless solid with a yield of 59%.

25.1 g of the dodecylammonium dodecylglucaramide was dissolved in 1.28 kg of tetrahydrofuran (THP). 25.9 g of Amberlyst® 15 in hydrogen form was added and the mixture was stirred at 40° C. for 6 h. After cooling to 20° C., the ion exchanger was filtered off and washed with THF (2×50 mL). The filtrate was dried in vacuum at 418 mbar and 53° C. Recrystallization from THF and MTBE gave an off-white solid (3.63 g) of dodecylglucaramidolactone ((2R)-2-[(2S, 3R,4S)-3,4-dihydroxy-5-oxo-tetrahydrofuran-2-yl)-N-dodecyl-2-hydroxy-acetamide) with a 19% yield.

Example 3

60.4 g of sodium glucaro-6,3-lactone was dissolved in 410 g of water and stirred at 33° C. until dissolved. 76.5 g of Octadec-9-enylamine was added dropwise into 55.6 g of methanol over a duration of 30 min with stirring at 400 rpm. The dropping funnel was rinsed with additional 7 g of methanol. During the addition, the mixture was heated up by 10° C. After complete addition, the reaction mixture was heated to 75° C. and stirred for 4 h. A colorless foam formed during heating after 20 min above 58° C. The precipitate was collected by filtration over a glass filter P3 and washed with cold methanol (2×50 mL) and dried in vacuum to obtain 106 g of octadecenylammonium octadecenylglucaramide (octadecenylammonium (2R,3R,4R,5S)-6-(octadecenylamino)-2,3,4,5-tetrahydroxy-6-oxohexanoate) as a colorless solid with a yield of 51%.

105 g of the octadecenylammonium octadecenylglucaramide was dissolved in 1.32 kg of tetrahydrofuran. 106 g of Amberlyst® 15 in hydrogen form was added and the mixture was stirred at 40° C. for 6 h. After cooling to 20° C., the ion exchanger was filtered off and washed with THF (2×50 mL). The filtrate was dried in vacuum at 200 mbar and 60° C. Thereafter, the filtrate was kept overnight at 0.5 mbar, thereby giving 58.4 g of octadecenylglucaramidolactone ((2R)-2-[(2S,3R,4S)-3,4-dihydroxy-5-oxo-tetrahydrofuran-2-yl]-2-hydroxy-N-octadecenyl-acetamide) as a light brown solid with a yield of 90%.

The invention claimed is:

1. A process for preparing D-glucaro-6,3-lactone monoamide, comprising the steps of:
A) adding an amine of general formula (I)

(I), wherein
$R_1$ denotes unsubstituted, linear or branched, alkyl or alkenyl having 4 to 22 carbon atoms,
to an aqueous solution of sodium glucaro-6,3-lactone and heating at a temperature in the range of ≥40° C. to ≤90° C., to obtain a compound of general formula (II)

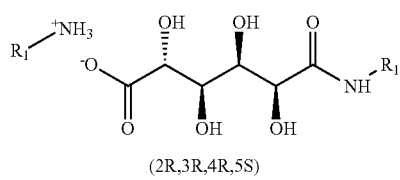
(II)

wherein,
$R_1$ denotes unsubstituted, linear or branched, alkyl or alkenyl having 4 to 22 carbon atoms,
and
B) treating the compound of general formula (II) with an acidic cation exchanger to obtain a compound of general formula (III)

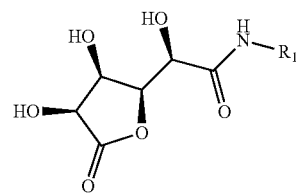
(III)

wherein,
$R_1$ denotes unsubstituted, linear or branched, alkyl or alkenyl having 4 to 22 carbon atoms;
wherein in step (A) the amine of general formula (I) is present as a mixture with at least one alcohol solvent selected from the group consisting of ethanol, methanol, n-butanol, iso-butanol, sec-butanol, n-propanol, iso-propanol, pentanol and hexanol; and
wherein in step (B) the compound of general formula (II) is dissolved in at least one ether solvent selected from the group consisting of tetrahydrofuran, 2-methyltetrahydrofuran, 1,4-dioxane, diethyl ether, diisopropyl ether, di-n-propyl ether, di-n-butyl ether, methyl-tert-butyl ether, diisobutyl ether, tetrahydropyran and dimethoxy-ethane.

2. The process according to claim 1, wherein $R_1$ denotes unsubstituted, linear or branched, alkyl or alkenyl having 6 to 18 carbon atoms.

3. The process according to claim 1, wherein in step (A) weight ratio between the at least one polar solvent and the amine of general formula (I) is in the range of ≥1:5 to ≤5:1.

4. The process according to claim 1, wherein in step (A) molar ratio between the amine of general formula (I) and the aqueous solution of the salt of D-glucaro-6,3-lactone is in the range of ≥1:1 to ≤10:1.

5. The process according to claim 1, wherein in step (A) the compound of general formula (II) is obtained by:
(A1) heating a mixture comprising the amine of general formula (I) and the aqueous solution of the salt of D-glucaro-6,3-lactone at a temperature in the range of ≥40° C. to ≤90° C. to obtain a precipitate,
(A2) filtrating the precipitate of step (A1) and washing with the at least one polar solvent to obtain a crude mixture and a mother liquor,
(A3) optionally storing the mother liquor of step (A2) at a temperature in the range of ≥0° C. to ≤30° C. for a period in the range of ≥8 h to ≤15 h to obtain a crude mixture, and
(A4) drying the crude mixture of step (A2) or optionally step (A3) to obtain the compound of general formula (II).

6. The process according to claim 1, wherein in step (B) the weight ratio between the acid and the compound of general formula (II) is in the range of ≥1:10 to ≤10:1.

7. The process according to claim 1, wherein in step (B) a temperature in the range of ≥10° C. to ≤60° C. is provided.

8. The process according to claim 1 further comprising the step of:
(C) drying the compound of general formula (III) obtained in step (B).

9. The process according to claim 1, wherein the step (B) further comprises a compound of general formula (IV)

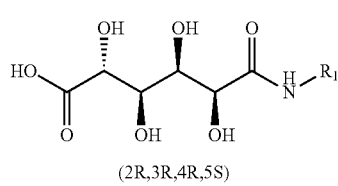

(IV)

(2R,3R,4R,5S)

wherein,

R₁ denotes unsubstituted, linear or branched, alkyl or alkenyl having 4 to 22 carbon atoms.

10. The process according to claim 8, wherein in step (A4) and step (C) the drying is carried out, independently of one another, under vacuum pressure in the range of ≥0.1 mbar to ≤500 mbar and at a temperature in the range of ≥20° C. to ≤80° C.

11. The process according to claim 1, wherein the at least one alcohol solvent is methanol.

12. The process according to claim 1, wherein the at least one ether solvent is selected from the group consisting of tetrahydropyran, tetrahydrofuran, and combinations thereof.

* * * * *